US012806035B2

(12) United States Patent
Caratsch

(10) Patent No.: US 12,806,035 B2
(45) Date of Patent: Nov. 24, 2026

(54) EXPANDABLE AND FLEXIBLE INTERVERTEBRAL IMPLANT

(71) Applicant: Alexander Caratsch, Trelex (CH)

(72) Inventor: Alexander Caratsch, Trelex (CH)

( * ) Notice: Subject to any disclaimer, the term of this patent is extended or adjusted under 35 U.S.C. 154(b) by 457 days.

(21) Appl. No.: 18/558,204

(22) PCT Filed: Mar. 30, 2022

(86) PCT No.: PCT/CH2022/050008
§ 371 (c)(1),
(2) Date: Oct. 31, 2023

(87) PCT Pub. No.: WO2022/232957
PCT Pub. Date: Nov. 10, 2022

(65) Prior Publication Data

US 2024/0216147 A1 Jul. 4, 2024

(30) Foreign Application Priority Data

May 2, 2021 (CH) ........................................ 476/21
Jun. 1, 2021 (CH) ........................................ 639/21
(Continued)

(51) Int. Cl.
*A61F 2/44* (2006.01)
*A61F 2/30* (2006.01)

(52) U.S. Cl.
CPC .... *A61F 2/446* (2013.01); *A61F 2002/30224* (2013.01); *A61F 2002/30471* (2013.01);
(Continued)

(58) Field of Classification Search
CPC ........ A61F 2/442; A61F 2/4455; A61F 2/446; A61F 2002/4415; A61F 2002/448; A61F 2002/4485
(Continued)

(56) References Cited

U.S. PATENT DOCUMENTS 4,309,777 A 1/1982 Patil
4,681,590 A 7/1987 Tansey
(Continued)

FOREIGN PATENT DOCUMENTS

DE 10130825 A1 3/2002
DE 10123124 C1 12/2002
(Continued)

OTHER PUBLICATIONS

International Search Report dated Jul. 15, 2022, for PCT Application No. PCT/CH2022/050008, filed on Mar. 30, 2022, 3 pages.
(Continued)

*Primary Examiner* — Eduardo C Robert
*Assistant Examiner* — Christina Negrellirodriguez
(74) *Attorney, Agent, or Firm* — Girma Wolde-Michae

(57) ABSTRACT

A dynamically morphing intervertebral implantable device modularly configurable and resiliently adjustable under compressive loads generated between an upper and lower vertebra is disclosed. Specifically, the configurability of the structure enables to effect variable volume and area for safe insertion and secure implantation of the device with the attendant advantage for segment stabilization between the upper and lower vertebrae. Various geometric bodies including stowed or non-stowed structural elements integrated therewith are disclosed. The geometric bodies include a prismatic body, conical body, cylindrical body, and any combination thereof. The geometric bodies including the stowed or non-stowed structural elements are modularly configurable having various sizes and dimension to accommodate a range of intervertebral spaces in order to provide a tailored fit for individual patient anatomies. The variable area and volume enable the device to have a secure and stable position within the intervertebral space thereby preventing detachment or displacement post implantation.

20 Claims, 13 Drawing Sheets

(30) Foreign Application Priority Data

| | | |
|---|---|---|
| Jun. 18, 2021 | (CH) | 716/21 |
| Aug. 4, 2021 | (CH) | CH070136/2021 |
| Aug. 10, 2021 | (CH) | CH070155/2021 |
| Sep. 21, 2021 | (WO) | PCT/CH2021/050021 |
| Feb. 18, 2022 | (CH) | CH000164/2022 |

(52) U.S. Cl.
CPC ................. *A61F 2002/3054* (2013.01); *A61F 2002/30579* (2013.01); *A61F 2002/30593* (2013.01)

(58) Field of Classification Search
USPC ............................................ 623/17.11–17.16
See application file for complete search history.

(56) References Cited

U.S. PATENT DOCUMENTS

| | | | | |
|---|---|---|---|---|
| 5,123,926 | A | 6/1992 | Pisharodi | |
| 5,653,763 | A | 8/1997 | Errico et al. | |
| 6,063,121 | A | 5/2000 | Xavier et al. | |
| 6,102,950 | A | 8/2000 | Vaccaro | |
| 6,126,689 | A * | 10/2000 | Brett | A61F 2/4455 623/17.15 |
| 7,270,680 | B2 | 9/2007 | Ralph et al. | |
| 7,563,286 | B2 | 7/2009 | Gerber et al. | |
| 7,780,733 | B2 | 8/2010 | Carver et al. | |
| 9,795,493 | B1 | 10/2017 | Bannigan | |
| 2002/0116064 | A1* | 8/2002 | Middleton | A61F 2/446 623/17.16 |
| 2003/0009223 | A1 | 1/2003 | Fehling et al. | |
| 2003/0187436 | A1 | 10/2003 | Bolger et al. | |
| 2005/0027362 | A1 | 2/2005 | Williams et al. | |
| 2005/0049590 | A1 | 3/2005 | Alleyne et al. | |
| 2005/0113916 | A1 | 5/2005 | Branch | |
| 2005/0209698 | A1 | 9/2005 | Gordon et al. | |
| 2006/0030943 | A1* | 2/2006 | Peterman | A61F 2/447 623/17.11 |
| 2006/0224241 | A1* | 10/2006 | Butler | A61F 2/446 623/17.11 |
| 2007/0191958 | A1 | 8/2007 | Abdou | |
| 2008/0004704 | A1 | 1/2008 | Katz | |
| 2008/0177389 | A1 | 7/2008 | Parrish | |
| 2010/0010633 | A1* | 1/2010 | Kohm | A61F 2/447 623/17.11 |
| 2010/0161061 | A1 | 6/2010 | Hunt | |
| 2010/0185290 | A1* | 7/2010 | Compton | A61F 2/4455 623/17.11 |
| 2012/0016480 | A1 | 1/2012 | Gerber et al. | |
| 2012/0150300 | A1 | 6/2012 | Nihalani | |
| 2012/0271423 | A1 | 10/2012 | Wallenstein et al. | |
| 2013/0166030 | A1 | 6/2013 | Biedermann et al. | |
| 2013/0197647 | A1* | 8/2013 | Wolters | A61F 2/442 623/17.16 |
| 2013/0310935 | A1 | 11/2013 | Swann | |
| 2014/0012383 | A1 | 1/2014 | Triplett et al. | |
| 2014/0018924 | A1 | 1/2014 | Mcmanus et al. | |
| 2015/0230929 | A1 | 8/2015 | Lorio | |
| 2017/0216051 | A1 | 8/2017 | Dewey | |
| 2017/0333205 | A1 | 11/2017 | Joly et al. | |
| 2019/0307577 | A1 | 10/2019 | Predick et al. | |
| 2019/0336299 | A1 | 11/2019 | Bernard et al. | |
| 2020/0093603 | A1* | 3/2020 | Manwill | A61F 2/447 |
| 2023/0270561 | A1 | 8/2023 | Caratsch | |

FOREIGN PATENT DOCUMENTS

| | | | |
|---|---|---|---|
| EP | 0637439 | A1 | 2/1995 |
| EP | 0664994 | A1 | 8/1995 |
| EP | 1273276 | A2 | 1/2003 |
| EP | 1699389 | A1 | 9/2006 |
| EP | 1996093 | A2 | 12/2008 |
| EP | 2910219 | A1 | 8/2015 |
| FR | 1651637 | A1 | 2/2016 |
| WO | WO9531158 | A1 | 11/1995 |
| WO | WO9640016 | A2 | 12/1996 |
| WO | WO9700054 | A1 | 1/1997 |
| WO | WO9848738 | A1 | 11/1998 |
| WO | WO9942062 | A1 | 8/1999 |
| WO | WO0182844 | A2 | 11/2001 |
| WO | WO02089701 | A2 | 11/2002 |
| WO | WO2004080356 | A2 | 9/2004 |
| WO | WO2005/092250 | A1 | 10/2005 |
| WO | WO2006/134262 | A1 | 12/2006 |
| WO | WO2007/079021 | A2 | 7/2007 |
| WO | WO2015087285 | A1 | 6/2015 |
| WO | WO2018/078148 | A1 | 5/2018 |
| WO | WO2019/173130 | A1 | 9/2019 |
| WO | WO2020/163278 | A1 | 8/2020 |
| WO | WO2022/232957 | A1 | 11/2022 |
| WO | WO2022/061477 | A9 | 1/2023 |

OTHER PUBLICATIONS

Written Opinion of the International Searching Authority dated Jul. 15, 2022, for PCT Application No. PCT/CH2022/050008, filed on Mar. 30, 2022, 5 pages.

* cited by examiner

EXPANDABLE AND FLEXIBLE INTERVERTEBRAL IMPLANT

CROSS REFERENCE OF RELATED APPLICATION(S)

The present application is the National phase application of the international PCT Patent Application PCT/CH2022/050008 filed on Mar. 30 2022, which claims priority from:

- Swiss Application No.: 00476/21, filed on May 2, 2021,
- Swiss Application No.: 00639/21, filed on Jun. 1, 2021,
- Swiss Application No.: 00716/21, filed on Jun. 18, 2021,
- Swiss Application No.: CH070136/2021, filed on Aug. 4, 2021,
- Swiss Application No.: CH070155/2021, filed on Aug. 10, 2021,
- Swiss Application No.: PCT/CH2021/050021, filed on Sep. 21, 2021 and
- Swiss Application No.: CH 000164/2022, filed on Feb. 18, 2022, the disclosures of which are incorporated by reference herein in its entireties as part of the present application.

The present invention relates to the medical field, and more particularly to an expandable and flexible intervertebral implant.

Certain pathologies of the spinal column, such as degenerated discs, facet diseases, and dislocation of vertebrae, compromise the support capacity of the column and the sharing of the load.

The treatment of such pathologies in their advanced stages is achieved by various stabilization systems with intra-discal implants such as interbody cages, which are typically coupled with extra-discal systems, which combine the use of vertebral screws and plates or rods to rigidly connect the two adjoining vertebrae. Such intra-discal implants have significantly improved the treatment of pathologies of the spinal column, by restoring the intervertebral space, which results in the decompression of the nerve roots and the acceleration of bony fusion of the adjoining vertebrae together.

Impactation cages represent an important category among interbody cages. These cages, which have a substantially parallelepiped shape, are inserted between the vertebrae by impactation. The downside of these cages is the difficulty of their insertion into the intervertebral space through narrow access routes using various surgical approaches, such as posterior, transforaminal, postero-lateral, lateral, antero-lateral and anterior approaches, in particular when interbody cages need to maximize contact surfaces with adjacent vertebrae in order to optimize the load sharing with the two adjacent vertebrae and reproduce the natural lordosis in the lumbar spine.

In order to overcome these challenges, interbody cages which expand in situ have been developed, among which are expandable cages where the increase of the volume of the cages within the adjoining vertebrae is achieved: for instance, US 2017/216051, U.S. Ser. No. 10/383,743B2, EP1645248A1, US20120109319 and U.S. Ser. No. 10/575,966B2 describe inventions where the intervertebral cages expand their height. Additional references describe cages with a pivoting member directly engaging vertebrae and increasing the separation space between two vertebrae: U.S. Ser. Nos. 13/877,851, 12/171,165, 11/276,345, 11/394,719, 09/350,984, 13/941,095, 13/605,751, 13/667,551, 13/095,634, 12/993,960, 8,187,332, and 15/739,696. Some of the references describe cages which comprise a mobile member pivoting around an axis on a longitudinal axis of another component. Among these references, U.S. Ser. No. 12/171,165 describes a mobile member which, when pivoted within a stationary element, causes flexible members to unwind outward the stationary member, thus increasing the volume of the cage. U.S. Ser. No. 15/739,696 describes a mobile member which, when pivoted within a fixed element, directly extends outward of the stationary element. The expanded volumes for the cages in these references reflect uneven increases of form factors and do not increase the actual perimeter of the contact surfaces of the cages with the adjoining vertebrae. Further, U.S. Pat. No. 6,395,031, US 2011/0276141, US 2019/336299, US 2019/307577, U.S. Pat. No. 7,318,839B2, U.S. Ser. No. 10/940,016B2, U.S. Ser. No. 10/898,340B2, US20200281739A1 and U.S. Pat. No. 9,795,493 provide examples of intervertebral cages expanding laterally to increase the contact surface between the implant and the adjoining vertebrae, and both U.S. Pat. Nos. 9,433,510 and 9,707,095B2 disclose intervertebral cages expanding both in height, to increase the separation space between two vertebrae, and laterally, to increase the perimeter of the contact surface between the cage and the vertebrae: however, in such cited references, the expansions are not achieved by any component of the interbody cage which pivotally engage the vertebrae to durably expand the contact surface between the vertebrae and the interbody cage.

The purpose of the present invention is to provide an interbody cage for the spinal column which increases the volume of the interbody cage from a first wrapped, or rolled or stowed configuration into a second unwrapped, unrolled or deployed configuration such that the perimeters of the contact surfaces between the interbody cage and the vertebrae increase from the stowed configuration to the deployed configuration of the cage. The interbody cage of the invention is structured as an assembly of at least two components: one base member (also named a cage body), which receives the pivoting means of a pivoting member (also named an extension member), structured to pivot around an axis located on the base member. The purpose of the extension member is to pivotally engage one or both vertebrae of a vertebral segment to expand the perimeter of contact surface of the interbody cage with one vertebra or both vertebrae, or to increase the height of the interbody cage and the separation space between the two vertebrae, or to increase both the perimeters of the contact surface of the interbody cage with the vertebrae and its height. The deployment of the extension member increases the form factor of the cage to provide broader and more stable surfaces of contact with the vertebrae.

In preferred embodiments, the extension member is structured to be wrapped or rolled around a portion of the cage body (or vice versa) in a first configuration, and to pivotally engage the two vertebrae and unwrap or unroll and deploy into a second configuration by the pivoting in reverse directions of the cage body and of the extension member while both the cage body and the extension member remain engaged with the vertebrae. In other embodiments, the extension member may be arranged with cambered ribbons, rings split with one strand, flattened hooks, mesh-frames and solid block structures which are stowed, rolled or wrapped inside of the cage body in a first configuration for the insertion between two vertebrae and are then deployed or unrolled or unwrapped outwards of the cage body to separate adjoining vertebrae in a second configuration, such deployment being actuated by pivoting the extension member around an axis of rotation configured within the cage body or on a surface or on a lateral side of the cage body.

Conversely, the cage body and extension members may also be arranged with flat rings, split rings, flat hooks, mesh-frames and solid block structures, unwrapping or rolling out or deploying out of an extension member.

The invention also covers methods of deploying the extension member after the insertion of the cage, in the cage's stowed configuration, between two vertebrae. According to a first method, as the extension member is pivoted, the deploying extension member is pushing against one of the vertebrae which serves as fulcrum against the lever of the shaft which serves as pivoting axis. The pressure of the extension member against the vertebra exceeds the compression force of the two vertebrae against the body of the cage and causes the body of the cage to pivot in the reverse direction to the direction of the pivoting extension member: according to that method, the pivoting of the extension member alone causes the full deployment of the cage without the need of simultaneously pivoting the body of the cage with an instrument. According to a second method to deploy a cage comprising of an oblong shaped body and an oblong shaped extension member, after the insertion of the cage between two vertebrae with its larger dimensions engaging the vertebrae, the oblong shaped body and oblong shaped extension member are simultaneously pivoted in reverse directions, which causes each of the two extremities of the respective body and extension member to diverge from one another creating a pressure against the vertebrae of the segment, and distracting them until the long dimension of each of the body and the extension member are fully deployed maintaining that new separation distance between the two vertebrae and having simultaneously expanded the cage also laterally. A third method of delivery of a cage comprising a body and two extension members consists in introducing the cage in a fully stowed configuration with a body and with two extension members which are essentially aligned, and deploying only one of the two extension members or deploying them both in an asynchronized manner while pivoting the body, such that in a deployed configuration, one extension member is upside down relative to the other extension member.

All the embodiments of the invention may be configured with cage bodies and extension members structured to provide a damping characteristic to the implant between the two adjoining vertebrae, to mimic the natural structure of cancellous bone, to prevent subsidence around the cage and to stimulate the bone growth around and through the inter-body cage.

The invention may also be used to separate two spinous processes and lock the processes in a distracted position.

The embodiments of the invention may apply to any constructs separating bones and/or for the fusion of any bones.

The characteristics of the invention will appear more clearly from the description of various embodiments and their variations, which are solely provided as examples and are not limitative, and in which references will notably be made to the anterior end or frontal or front end of the cage or body, thus defining that part of the cage which is adjusted against the vertebrae just before the introduction of said cage or body into the interbody space, and to the posterior end or rear-end of the cage body, which shall define the part of the cage opposite the anterior end or front end. The words "pivoted" and "rotated" are used within the same meaning, to describe a motion around an axis. The description of these various embodiments refers to the attached schematic Figures in which:

Figure 1:
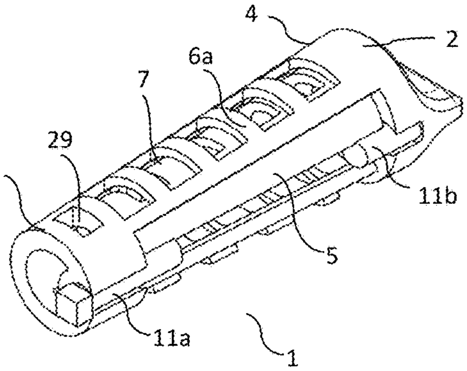
FIG. 1 represents a perspective rear view of the cage of the first embodiment in a stowed configuration.
Figure 2:
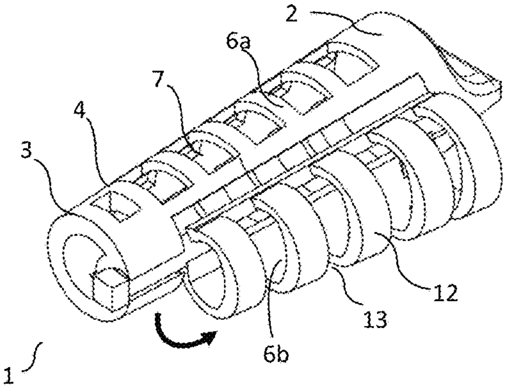
FIG. 2 represents the same perspective rear view of the cage in FIG. 1 with its extension member in a deployed configuration.
Figure 3:
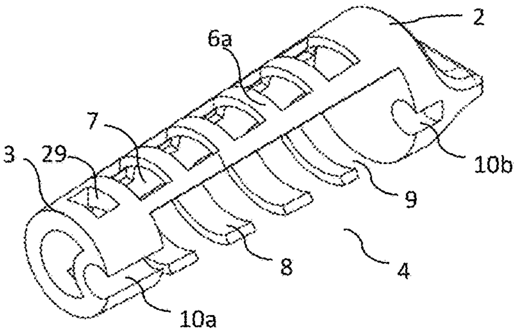
FIG. 3 represents a perspective rear view of the body of the cage of the first embodiment.
Figure 4:
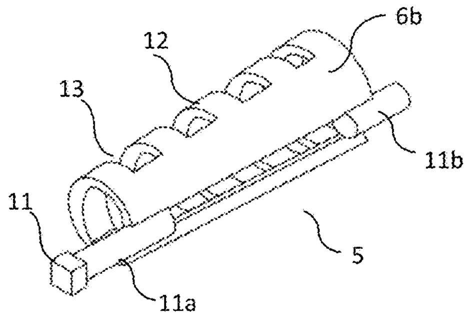
FIG. 4 represents a perspective rear view of the extension member of the cage of the first embodiment.

According to FIGS. 1 and 2, the first embodiment of the invention describes an interbody cage assembly (or cage) 1, for delivery via a posterior or transforaminal surgical approach, with a base member or body 4 having an essentially cylindric cross-section, a front end 2 and a rear end 3. FIGS. 3 and 4 represent the two elements 4, 5 constituting the cage 1. As shown in FIG. 3, the cage body (or body) 4 comprising the front end 2 and the rear end 3 has an essentially cylindric cross-section and has a median part between the front end 2 and the rear end 3 arranged with a tubular structure 6*a*: The tubular structure 6*a* may be arranged with openings 7 and with cambered ribbons 8 separated by slots 9. Two channel sections 10*a*, 10*b* are arranged in the body 4 on a same axis: a first proximal channel section 10*a* in the periphery of the rear end 3 and a second distal channel section 10*b* in the periphery of the front end 2, to receive the pivoting shafts 11*a*, 11*b* of the extension member 5. According to FIG. 4, the extension member 5 is configured as a tubular structure 6*b* mounted on the proximal and distal shaft sections 11*a*, 11*b*. A portion of the tubular section 6*b* of the extension member is arranged with cambered ribbons 12 which are separated by slots 13.

The cambered ribbons 8, 12 of the cage 1 may have different thicknesses depending on the desired resistance to compression force or flexibility: such rigidity vs. flexibility may be modulated by differential thicknesses applied on the same cambered ribbon 8, 12: for instance a strengthened portion 14 may be arranged on the cambered ribbons 8, 12 on the cage 1's portions designed to sustain compression forces, while the thinner parts of the cambered ribbons 8, 12 are positioned on the cage 1's portions engaging the upper and lower vertebrae V1, V2 in order to share the load of such vertebral plates more evenly on such thinner bending surfaces of the cambered ribbons 8, 12.

Figure 26:
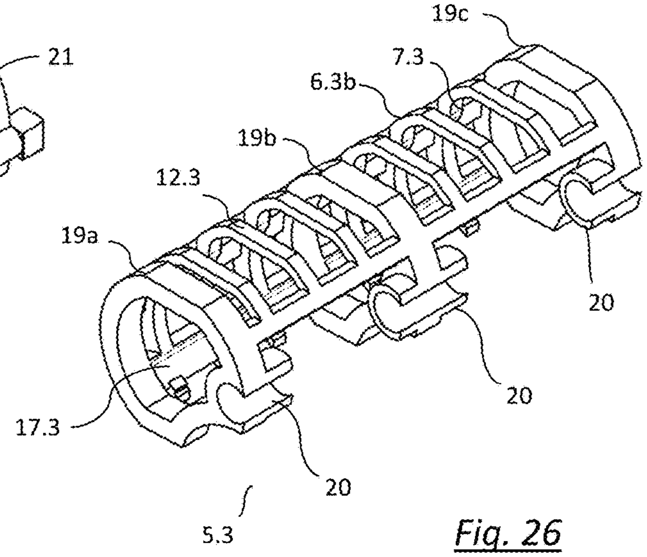
FIG. 26 represents a perspective front view of the extension member of the cage of the third variation of the second embodiment.
Figure 27:
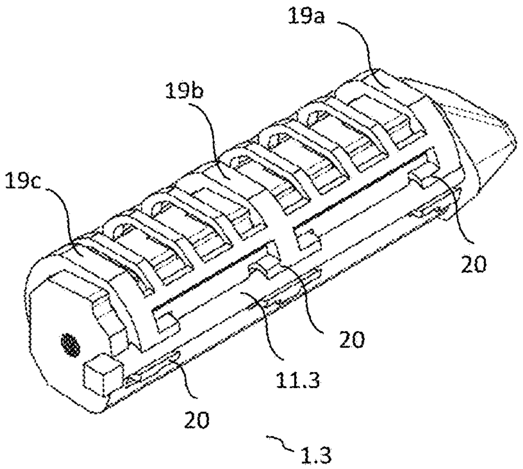
FIG. 27 represents a perspective rear view of the cage of the third variation of the second embodiment in a stowed configuration.
Figure 28:
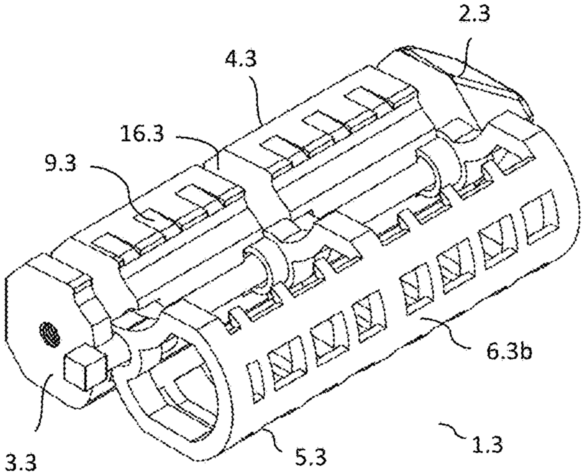
FIG. 28 represents a perspective rear view of the upside-down cage of the third variation of the second embodiment in a deployed configuration.

As shown in FIGS. 1 and 6 to 11 the relative diameters of the tubular structure 6*a* of the body 4 are superior to the relative diameters of the tubular structure 6*b* of the extension member 5, such that the extension member 5 is positioned within the body, or as may be described differently, the body 4 is superposed to and rolled or wrapped around the extension member 5. As shown in FIG. 26, in different embodiments and variations of the invention, the extension member 5.3 may be superposed to and rolled or wrapped around the body 4.3. The width of the cambered ribbons 12 of the extension member 5 is smaller than the width of the slots 9 arranged on the tubular structure 6*a* of the body 4, and the width of the cambered ribbons 8 of the body 4 is smaller than the width of the slots 13 arranged on the tubular structure 6*b* of the extension member 5.

Figure 5:
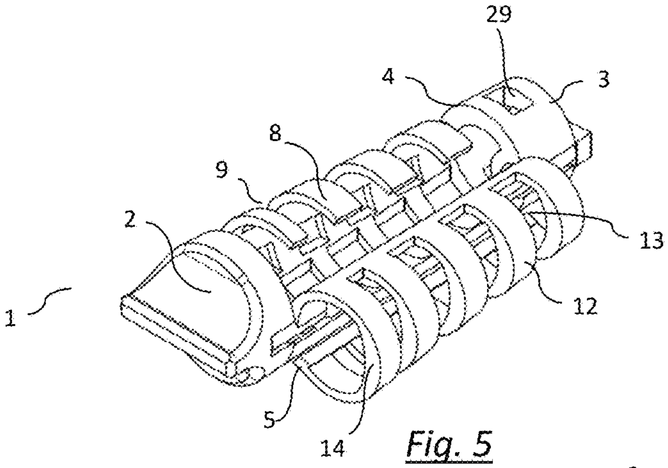
FIG. 5 represents a perspective front view of the cage in FIG. 2 in a deployed configuration.
Figure 6:
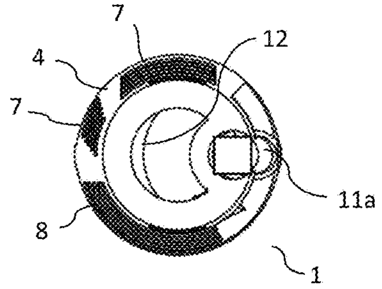
FIG. 6 represents a rear view of the cage of the first embodiment in a stowed configuration.
Figure 7:
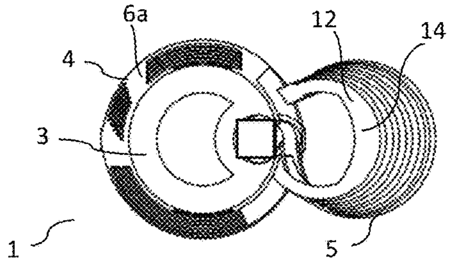
FIG. 7 represents a rear view of the cage in FIG. 6 in a deployed configuration.

FIGS. 1 and 6 describe the first configuration of the cage 1 comprising the body 4 and the extension member 5, where the extension member 5 is stowed within the body 4. FIGS. 2, 5 and 7 describe the second configuration of the cage 1, after the completion of the deployment (or unrolling or unwrapping) of the extension member 5 outwards of the body 4, to increase the cage 1's form factor from the first configuration of the cage 1 to this second configuration.

The advantage of this invention is that the access route for the cage 1 in its stowed configuration into the intervertebral space may be narrower, thus preserving the ligament, muscle, nerves and bone tissues from excessive resection.

Figure 8:
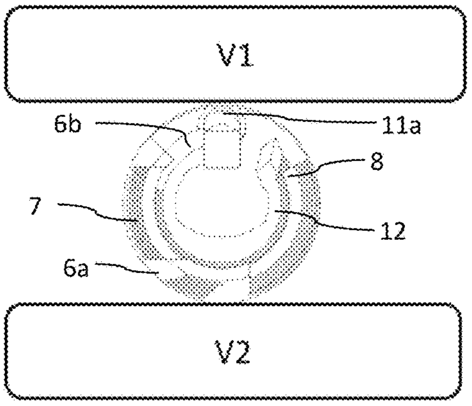
FIG. 8 represents a rear view of a cross-section of the cage of the first embodiment in a stowed configuration between two schematic vertebrae.
Figure 9:
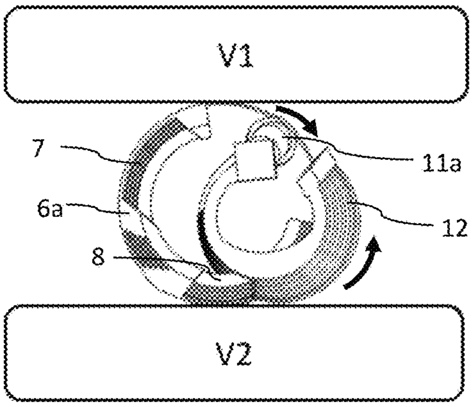
FIG. 9 represents the same cross-section of the cage as in FIG. 8 with a partially deployed extension member.
Figure 10:
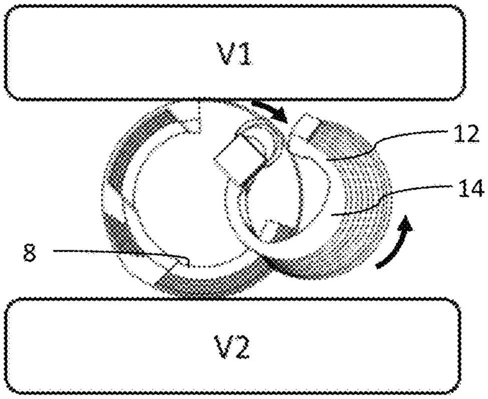
FIG. 10 represents the same cross-section of the cage as in FIGS. 8 and 9 with its extension member further deployed.

FIGS. 8 to 11 describe the method of deploying the cage 1 between two vertebrae V1, V2. The insertion of the cage 1 between two vertebrae V1, V2 is achieved by impaction by the means of any instrument affixed to the rear end 3 of the cage 1 for instance mounted to the openings 29 through the inside of the rear end 3 of the body 4, or from the external side. The instrument must also be capable of engaging and pivoting the proximal shaft 11*a* of the extension member, for instance the bolt 11*c* configured on the proximal shaft section 11*a*. Once the cage 1 has reached its desired position between two vertebrae V1, V2 as shown in FIG. 8, the deployment of the extension member 5 may be facilitated by applying the deployment method described in FIGS. 9 and 10, wherein the body 4 is pivoted approximately 90° between the vertebrae V1, V2 and simultaneously, the extension member 5 is pivoted approximately 90° in the reverse direction, through the actuation of its proximal shaft section 11*a*. Due to the narrower width of the cambered ribbons 8 on the body 4, relative to the width of the slots 13 in the extension member 5, and the narrower width of the cambered ribbons 12 on the extension member 5, relative to the width of the slots 9 in the body 4, the respective sets of cambered ribbons 8, 12 on one component may slide through the respective slots 9, 13 of the other component without impairing the deployment of the extension member 5, as shown in FIGS. 9 and 10.

Figure 11:
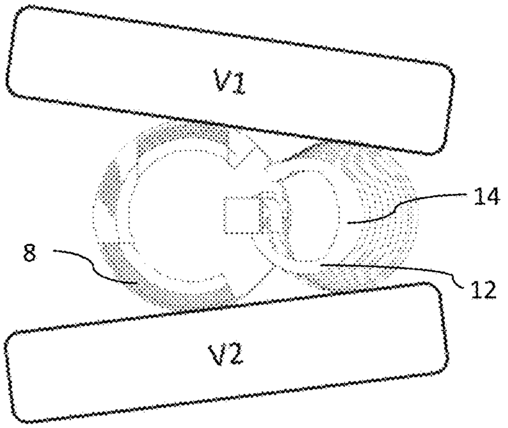
FIG. 11 represents the same cross-section of the cage as in FIGS. 8, 9 and 10 with its fully deployed extension member.

FIG. 11 represents the fully deployed extension member 5. The perimeter of the deployed cage 1, ranging from that portion of the tubular structure 6*a* and cambered ribbons 8 of the body 4 resting against the vertebrae to that portion of the tubular structure 6*b* and cambered ribbons 12 of the extension member 5 resting against the vertebrae, has significantly increased the perimeter of the contact surface of the cage 1 with the vertebrae V1, V2 compared to the contact surface of the body 4 alone with those vertebrae, in the stowed configuration. Due to the smaller diameter of the extension member 5 relative to the diameter of the body 4, the deployed cage 1 generates an angle between the vertebrae V1, V2, which is beneficial for cages delivered through lateral, transforaminal or antero-oblique approaches.

As shown in FIG. 11, the openings 7 arranged in the tubular structures 6*a* of the body 4 are opened towards the vertebral endplate of the upper vertebra V1, while the slots 9, 13 of the body 4 and of the extension member 5 are facing the vertebral endplate of the lower vertebra V2, which enables graft inserted in the cage 1 to connect with the vertebrae. In addition, the edges of the cambered ribbons 8, 12 when pressed against the vertebrae V1, V2, represent an anchoring means against the migration of the cage 1.

Figure 12:
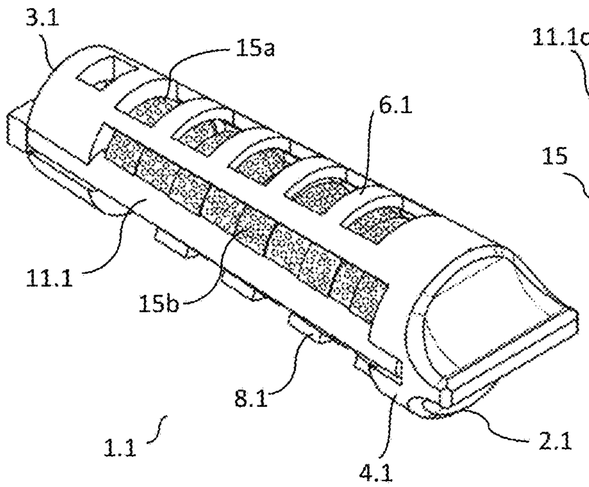
FIG. 12 represents a perspective front view of the cage of the second embodiment in a stowed configuration.
Figure 13:
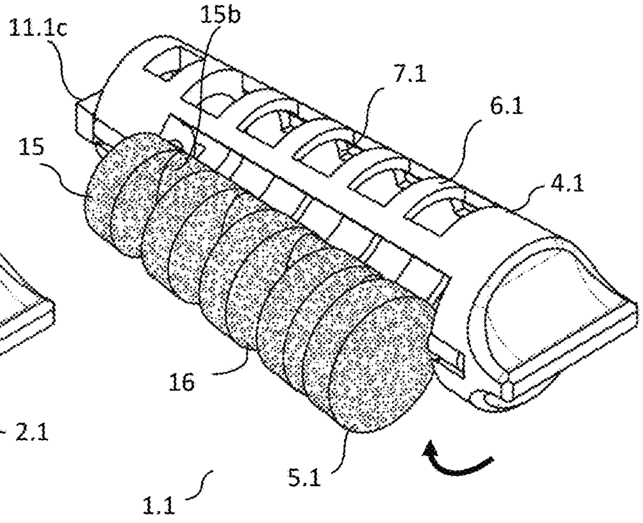
FIG. 13 represents the same perspective front view of the cage in FIG. 12 with its extension member in a deployed configuration.
Figure 14:
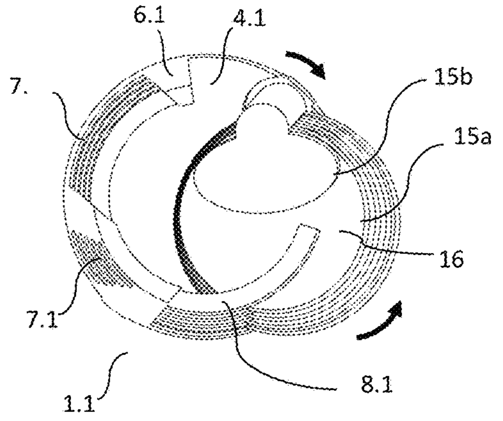
FIG. 14 represents a rear view of a cross-section of the cage of the second embodiment with a partially deployed extension member.
Figure 15:
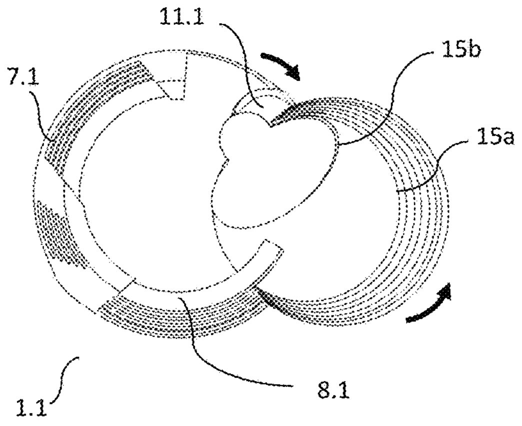
FIG. 15 represents the same cross-section of the cage as in FIG. 14 with a further deployed extension member.

FIGS. 12 and 13 represent the second embodiment of the invention of the cage 1.1, where the body 4.1 of the cage 1.1 is essentially similar to the body 4 of the first embodiment, but where the extension member 5.1 is made of compact blocks of material which may be made of serrated titanium, open pore metal alloy or coated PEEK. The extension member 5.1 is shaped in an alternating succession of round discs 15*a* separated by oval discs 15*b*. The oval discs 15*b* thus define crevasses 16 between a portion of the round discs 15*a*. The discs 15*a*, 15*b* are mounted on the shaft 11.1 of the axis. FIGS. 14 and 15 describe how the crevasses 16 play the role of the slots 13 of the extension member 5 of the cage 1 of the first embodiment, enabling the cambered ribbons 8.1 of the body 4.1 to slide between the round discs 15*a*.

Figure 16:
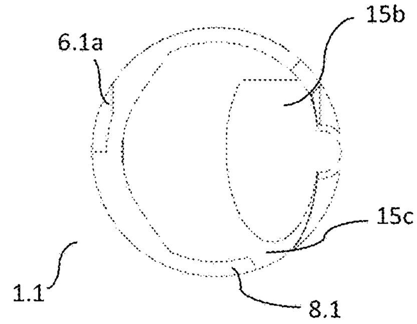
FIG. 16 represents a rear view of a cross-section of the first variation of the cage of the second embodiment with a stowed extension member.
Figure 17:
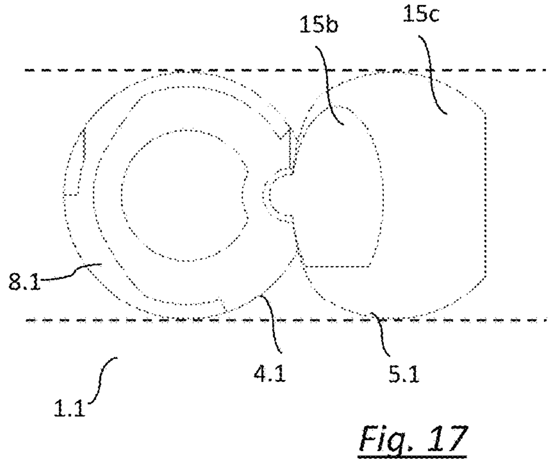
FIG. 17 represents the same cross-section of the cage of FIG. 16 with a fully deployed extension member.
Figure 18:
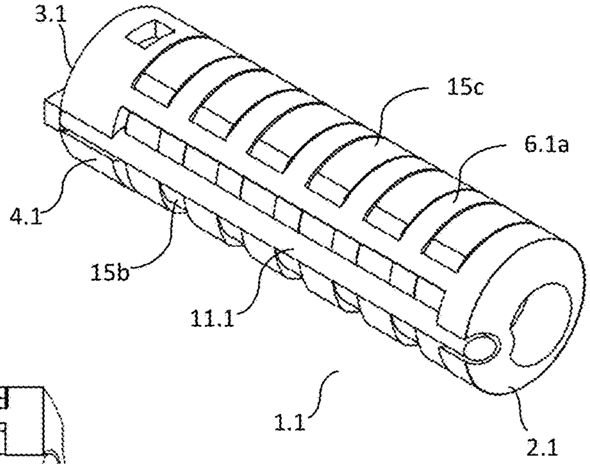
FIG. 18 represents a perspective front view of the first variation of the cage of the second embodiment in a stowed configuration.
Figure 19:
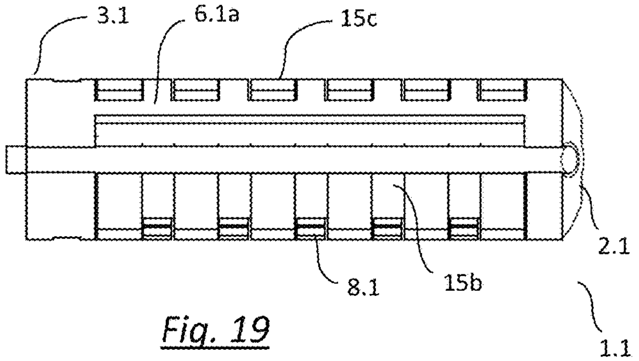
FIG. 19 represents a side view of the same cage as in FIG. 18.
Figure 20:
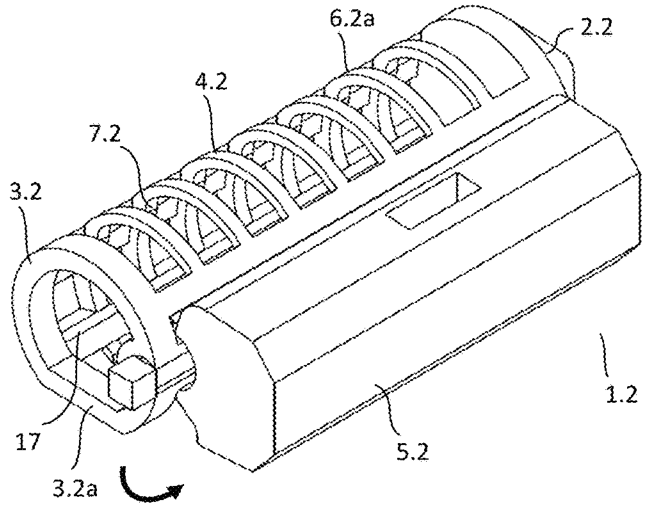
FIG. 20 represents a perspective rear view of the second variation of the cage of the second embodiment in a deployed configuration.

A first variation of the extension member 5.1 is shown in FIGS. 16 to 18, with oblong discs 15*c* mounted on the shaft 11.1 of the axis instead of round discs. The two ends of the longer dimension of these oblong discs 15*c* may protrude through the openings 7.1 and the slots 9.1 of the body 4.1 and be level with the external surface of the tubular structure 6.1*a* and of the cambered ribbons 8.1 of the body 4.1, as shown in FIGS. 18 and 19. The oval discs 15*b* in this variation have a chopped-off end in their longer dimension, in order to allow the unencumbered deployment of the extension member 5.1 by the extremities of the cambered ribbons 8.1 of the body 4.1. The advantage of this variation is to create two parallel planes between the upper and lower surfaces of the deployed cage 1.1 in contact with the upper and lower vertebrae V1, V2, as shown in FIG. 17. The cambered ribbon structure 12 of the extension member 5 of the first embodiment may also be arranged in an oblong shape instead of a round one to achieve the same objective as the extension member 5.1 of this variation of the second embodiment.

The cage 1.1 of this variation may be introduced between two vertebrae V1, V2 through a tube arranged with a beveled or wedged tip to distract the vertebrae. With such a delivery system, the body 4.1 of this variation does not require a wedged front end: as shown in FIG. 18, the body 4.1 has an essentially flat front end 2.1 without wedge and is arranged with an opening, which has the advantage of extending the length of the loading surface of the cage 1.1 of this variation and to enable graft material to fuse with the bone adjoining the front end 2.1.

A second variation of the second embodiment of a cage 1.2 is illustrated in FIGS. 20 to 24 and consists in a body 4.2 and an extension member 5.2 configured as a compact block of material mounted on a shaft 11.2. In this second variation, the body 4.2 has an open tubular structure 6.2*a* arranged with a front end 2.2 having one flattened part 2.2*a* and a rear end 3.2 in the shape of a ring also having a flattened part 3.2*a*. The tubular structure 6.2*a* has shorter cambered ribbons 8.2 than in the first variation of the second embodiment, with a connector 17 connecting all cambered ribbons 8.2 at a location towards their ends and extending to connect the cambered ribbons 8.2 to the front end 2.2 and to the rear end 3.2 of the body 4.2. The cambered ribbons 8.2 extend slightly beyond the connector 17 to represent stumps 18, which may help anchor the cage 1.2 after its deployment between two vertebrae V1, V2. The compact block of the extension member 5.2 has slots 16.2, which are the remnants of the crevasses 16 of the preceding variations, to avoid the clashing between the body 4.2 and the extension member 5.2 during the motion of the deployment of the cage 1.2.

Figure 21:
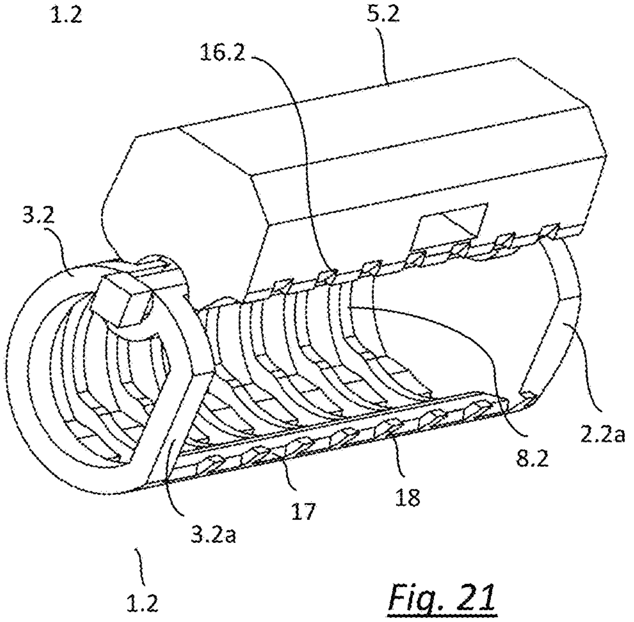
FIG. 21 represents a low-angle rear view of the same cage as in FIG. 20 in a deployed configuration.
Figure 22:
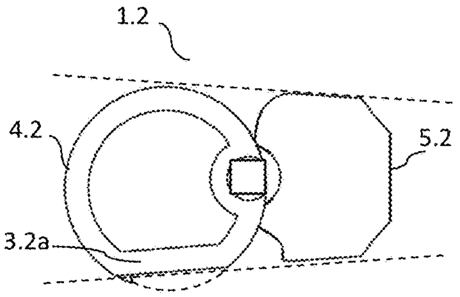
FIG. 22 represents a rear view of the same cage as in FIGS. 20 and 21 in a deployed configuration.

As shown in FIG. 21, the flattened part 2.2*a* of the front end 2.2 and flattened part 3.2*a* of the ring at the rear end 3.2, together with the connector 17, define three sides of the perimeter of an opening, in which a large amount of bone graft may be packed. This three-sides perimeter is closed by the flattened surface of the block component of the extension member 5.2. FIG. 22 describes how the larger diameter of the body 4.2 relative to the dimension of the cross-section of the extension member 5.2 has been offset by the flattened parts 2.2*a*, 3.2*a* of front and rear ends 2.2, 3.2, to define the desired angulation of the cage assembly 1.2. The variety of possible positioning and of angulations of these flattened parts 2.2*a*. 3.2*a* within the front and rear ends 2.2, 3.2 determine an increase or decrease of the desired angulation of the cage 1.2 regardless of the dimension of the diameter of the body 4.2 relative to the dimension of the cross-section of the extension member 5.2.

Figure 23:
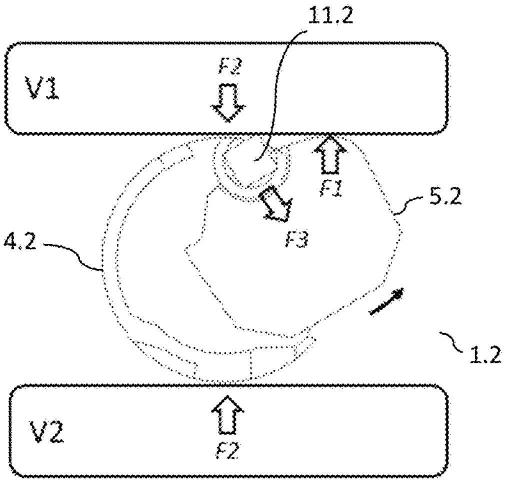
FIG. 23 represents a rear view of a cross section of the cage in FIGS. 20 to 22 between two schematic vertebrae with a partly deploying extension member.
Figure 24:
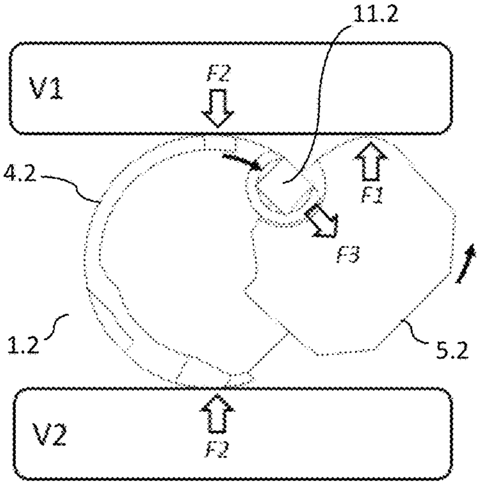
FIG. 24 represents the same rear view as in FIG. 23 with a further deploying extension member.
Figure 25:
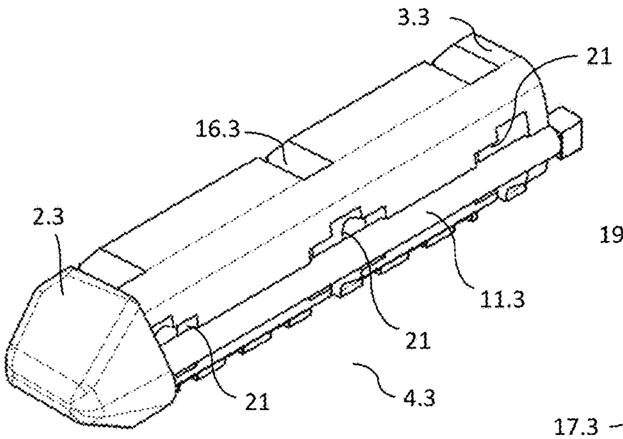
FIG. 25 represents a perspective front view of the body of the cage of the third variation of the second embodiment.

FIGS. 23 and 24 describe a method of deploying the extension member 5.2 of the cage 1.2 from a first stowed configuration into a second deployed configuration. The cage 1.2 is first inserted in the stowed configuration between two vertebrae until its final location, where the vertebrae V1, V2, exert a compression force “F2” on the body 4.2. According to FIG. 23, as the extension member 5.2 is pivoted outwards from the body 4.2, the deploying extension member 5.2 is pushing with force “F1” against the vertebra V1 which serves as fulcrum against the lever represented by the shaft 11.2 of the pivoting axis. If the pressure force “F1” exerted against the vertebra V1 by the extension member 5.2 exceeds the compression force “F2” of the two vertebrae V1, V2 against the body 4.2 of the cage 1.2, that pressure “F1” translates into force “F3” of the shaft 11.2 against the channel 10.2 in the body 4.2 and causes the body 4.2 to pivot in the reverse direction to the direction of the pivoting extension member 5.2, as shown in FIG. 24. According to that method, the pivoting of the extension member 5.2 alone causes the full deployment of the cage 1.2 to the stage represented in FIG. 22 for this embodiment, and represented in FIGS. 7 and 11 for the first embodiment, without the need to simultaneously pivot the body 4.2 of the cage 1.2 using an instrument.

FIGS. 25 to 29 represent a third variation of the second embodiment of the invention, where, unlike in the cases of the first embodiment and of the first and second variations of the second embodiment, the body 4.3 of the cage 1.3 is configured with cross-sectional dimensions that are smaller than the dimension of the diameter of the extension member 5.3, such that the extension member 5.3 is superposed to, and rolled or wrapped around the body 4.3; the body 4.3 is rolled out of the extension member 5.3 during the deployment of the cage 1.3.

The body 4.3 is arranged with four block-portions: a wedged front end 2.3, a flat rear-end 3.3 with a threaded hole to receive an instrument and two longitudinal portions. The four parts of the body 4.3 are mounted to the shaft 11.3, and additional bridging material connects each part to the next part to solidify the body 4.3. The four parts of the body 4.3 are separated by three crevasses 16.3.

The extension member 5.3 is made of an open tubular structure 6.3*b* which in comparison to the tubular structure 6.2*a* of the body 4.2 in the second variation of the second embodiment, is flattened on a portion of its surfaces, which defines a plane to rest against one of the vertebrae V1 or V2. The tubular structure 6.3*b* is mounted on three rings 19*a*, 19*b*, 19*c* at the proximal and distal ends of the tubular structure 6.3*b* and at its middle section; these rings have two opposite flattened parts which define two planes for resting against the two vertebrae V1, V2. The flattened parts of the three rings 19*a*, 19*b*, 19*c* have a curved portion arranged to avoid the clashing with the bridging material arranged between the four blocks of the body 4.3. The three flattened rings 19*a*, 19*b*, 19*c* of the extension member 5.3 are each configured with one sleeve 20 to rotatably attach the extension member 5.3 to the shaft 11.3 of the body 4.3. A clearance space 21 is arranged on each of the four parts of the body 4.3 to enable the sleeves 20 to pivot around the shaft 11.3. The sleeves 20 strengthen the connection between the body 4.3 and the extension member 5.3. The median flattened ring 19*b* contributes to the load sharing with the two vertebrae.

Figure 29:
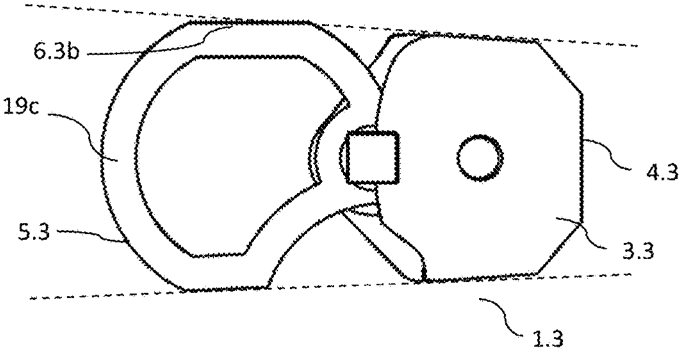
FIG. 29 represents a rear view of the cage of the third variation of the second embodiment in a deployed configuration.

FIG. 29 shows how the flattened surfaces of the tubular structure 6.3*b*, and of the three rings 19*a*, 19*b*, 19*c* increase the contact surface with the vertebrae V1, V2 and define an angle to the deployed cage 1.3.

Figure 30:
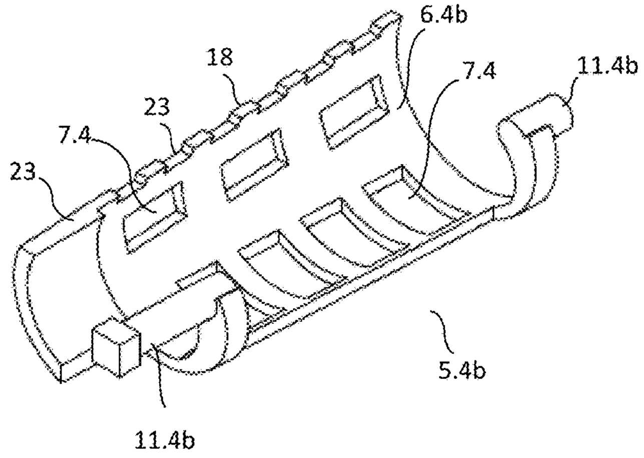
FIG. 30 represents a perspective rear view of the second extension member of the cage of the third embodiment.
Figure 31:
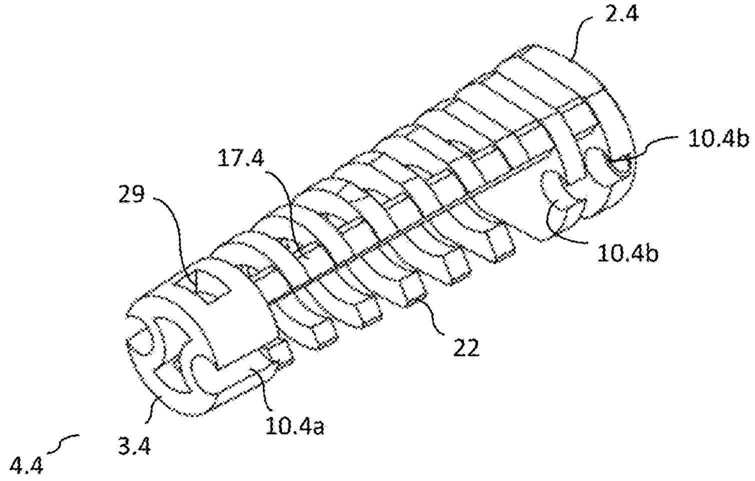
FIG. 31 represents a perspective rear view of the body of the cage of the third embodiment.
Figure 32:
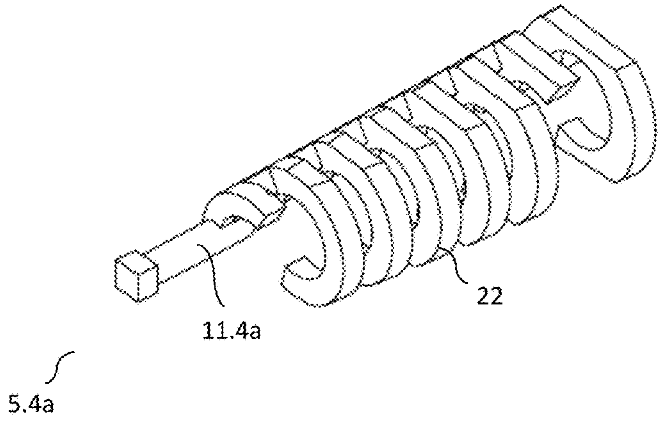
FIG. 32 represents a perspective rear view of the first extension member of the cage of the third embodiment.
Figure 34:
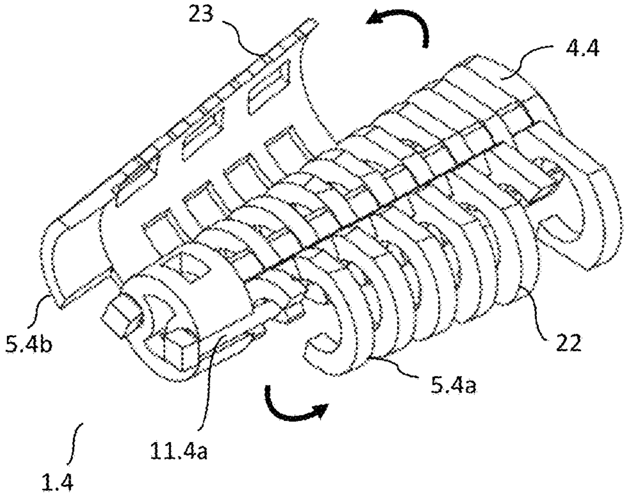
FIG. 34 represents the same view of the cage of the third embodiment as in FIG. 33 in a deployed configuration.
Figure 35:
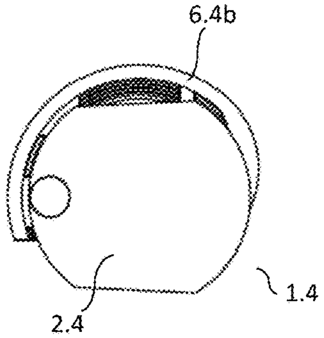
FIG. 35 represents a front view of the cage in FIG. 33 in a stowed configuration.
Figure 36:
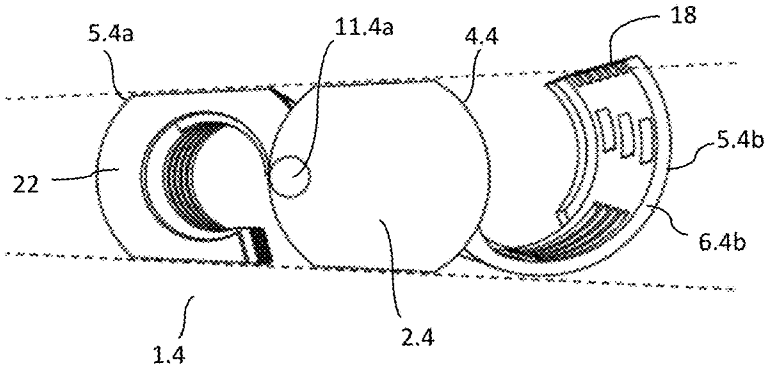
FIG. 36 represents a front view of the cage in FIG. 34 in a deployed configuration.
Figure 37:
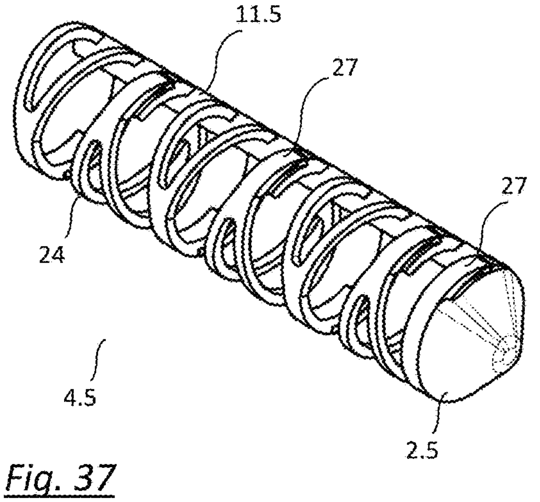
FIG. 37 represents a perspective front view of the body of the cage of the fourth embodiment.

A third embodiment of the invention is described in FIGS. 30 to 36, of a cage assembly 1.4 which may be used for a transforaminal surgical approach, comprising one body 4.4, a first extension member 5.4*a* and a second extension member 5.4*b*, each of said extension members 5.4*a*, 5.4*b* deploying on opposite sides of the body 4.4. According to FIG. 31, the body 4.4 is configured as a structure of parallel aligned hooks 22 held together and to the front end 2.4 and the rear end 3.4 of the body 4.4 by a connector 17.4. Some of the hooks 22 are flattened over a portion of two of their opposing surfaces to give the body 4.4 two obliquely angled planes, as also shown in FIG. 36. The rear end has openings 29 which may be used for engagement by an instrument. FIG. 32 describes the first extension member 5.4*a*, which has a similar structure to that of the body 4.4 of aligned and partly flattened hooks 22 held together by a connector 17.4. As shown in FIG. 30, the second extension member 5.4*b* has a tubular structure 6.4*b* similar to that of the extension member 5 of the first embodiment, and is arranged with a border 23 configured to rest against one adjoining vertebra and which has protruding stumps 18 to support the anchoring of the cage 1.4 in that vertebrae, as also shown in FIG. 36. Each of the two extension members 5.4*a*, 5.4*b* is configured with sections of shafts 11.4*a*, 11.4*b* to serve as pivoting axes within the channels 10.4*a*, 10.4*b*, 10.4*b*' of the body 4.4, positioned laterally of the body’s median axis.

Figure 33:
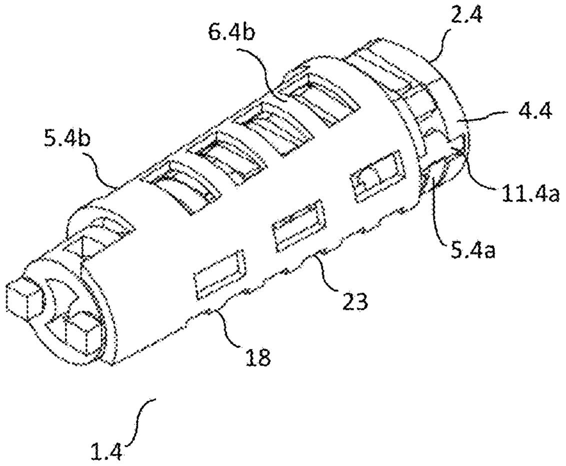
FIG. 33 represents a perspective rear view of the cage of the third embodiment in a stowed configuration.

FIGS. 33 and 35 represent the cage 1.4 in its wrapped configuration, where the hooks 22 of the first extension member 5.4*a* are stowed between the hooks 22 of the body 4.4, and where the second extension member 5.4*b* is rolled over or wrapped around the stowed assembly of the body 4.4 and first extension member 5.4*a*. In this configuration, the cage 1.4 may be inserted between two vertebrae V1, V2, either engaging them directly, or being delivered through a tube inserted between such vertebrae. FIGS. 34 and 36 represent the cage 1.4 in its deployed configuration, with both extension members 5.4*a*, 5.4*b* fully extended to separate two vertebrae V1, V2 in two oblique planes. The open tubular structure 6.4*b* of the second extension member 5.4*b* is beneficial where the intent is to provide the cage 1.4 a flexible or damping property between the two vertebrae V1, V2. In a variation, the tubular structure 6.4*b* may also be configured at its front and rear ends with flattened rings similar to the flattened rings 3.2*a*, 19*a*, 19*b*, 19*c* of some of the preceding embodiments and variations, in order to strengthen the structure of the second extension member 5.4*b* and increase its load sharing properties relative to the adjoining vertebra.

FIGS. 37 to 41 describe the fourth embodiment of the invention of a cage assembly 1.5 which may be used for a lateral surgical approach, comprising a body 4.5 structured with parallel aligned rings 24, and an extension member 5.5 configured as a tubular structure 6.5*b* made of aligned rings 25, partially connected together by a mesh structure 26. As best shown in FIGS. 37, 39, 41 and 43, the rings 24 of the body 4.5 are mounted on the shaft 11.5 by one branch at one end and are bifurcating into two branches mounted to the shaft 11.5 at the other end of the rings 24. These bifurcating branches of the rings 24 are increasing the load sharing surface relative to the vertebra V1, V2, against which they rest and, due to their smaller width, this bifurcating branches also offer to the 24 rings a damping characteristic and thus to the body 4.5 overall. Similarly, the mesh structure 26 arranged between the rings 25 of the extension member 5.5 support the stabilization of the rings 25 and yet remain relatively flexible to contribute to the damping feature of the extension member 5.5. In variations, the mesh structure 26 may also be arranged between the rings 24 of the body 4.5 and may also be substituted by a sheet of any material arranged between the rings 24, 25 of the body 4.5 and the extension member 5.5.

Figure 38:
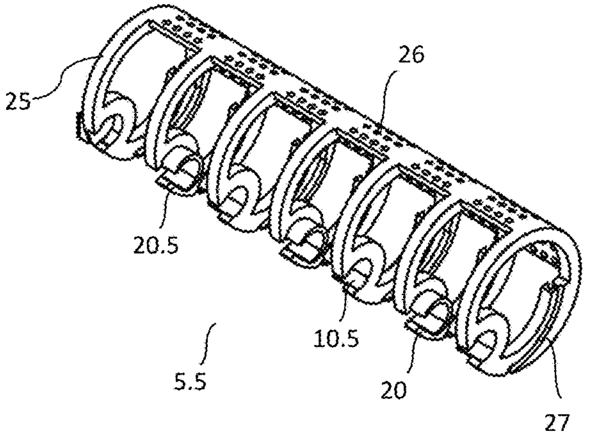
FIG. 38 represents a perspective front view of the extension member of the cage of the fourth embodiment.
Figure 39:
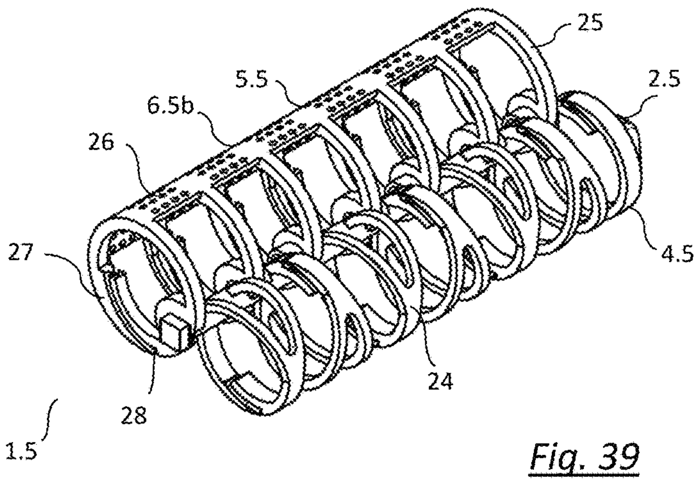
FIG. 39 represents a perspective rear view of the cage of the fourth embodiment in a deployed configuration.
Figure 42:
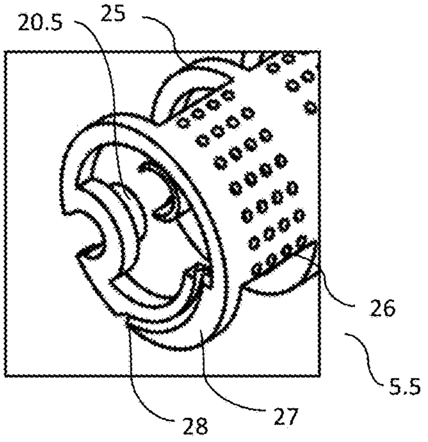
FIG. 42 represents a blow-up perspective view of the rear end of the extension member of the cage of the fourth embodiment.
Figure 43:
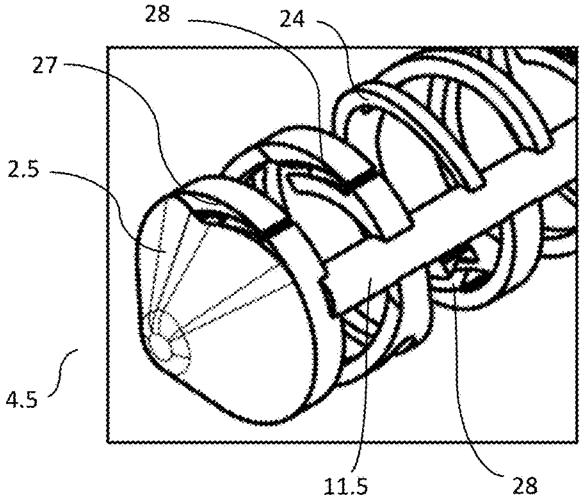
FIG. 43 represents a blow-up perspective view of the conical front end of the body of the cage of the fourth embodiment.
Figure 44:
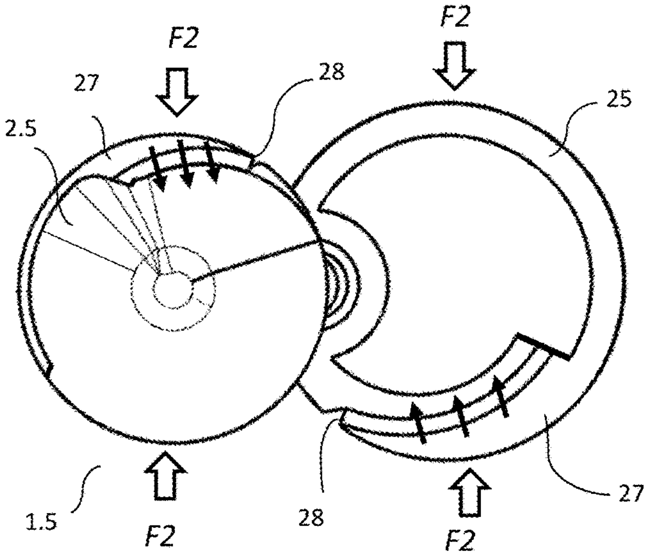
FIG. 44 represents a front view of the cage of the fourth embodiment in deployed configuration.

In order to further increase the damping feature of the body 4.5, the single branch portion of the rings 24 is splitting into two strands 27 separated from each other and thus creating a curved joint 28, as best described in FIGS. 43 and 44. Similarly, the rings 25 of the extension member 5.5 are also configured with separating strands 27 and joints 28, as shown in FIGS. 38, 39 and 42. According to FIG. 44, when the compression force "F2" is exerted against the cage 1.4, those strands 17 of the rings 24, 25 which rests against the vertebrae V1, V2 are closing the gap of the joints 28 with the opposing strands 27 of the rings 24, 25. The joints 28 described in the invention have a cross-section of a male triangular shape arranged on one strand 27 of the rings 24, 25 matching a female triangular shape, or gully, arranged in the other strand 27 of the rings 24, 25, in order to maintain a stable trajectory for the closure of the joint 28 and avoid dislodging of the respective strands. In variations, different shapes may be given to this cross-section, such as male/female round or oval, or a conical structure pressing into a conical depression and any other technically appropriate shapes.

According to FIGS. 43 and 44, the conic front end 2.5 of the body 4.5 is arranged with a base which splits in one strand 27 to create a joint 28 according to the same mechanism as described for the rings 24, 25, thus also providing specifically to the otherwise rigid front end 2.5 of the body 4.5, and thus to the body 4.5 along its whole length, a damping characteristic.

Figure 45:
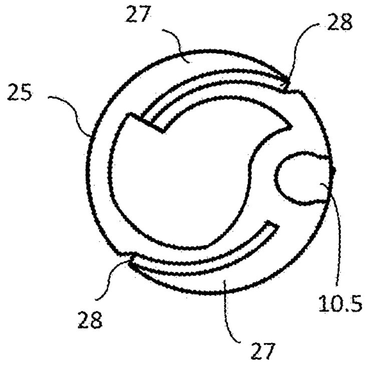
FIG. 45 represents a front view of one ring of the extension member of a variation of the fourth embodiment with two curved joints.

FIG. 45 describes a variation of the fourth embodiment, where one single ring 25 is configured with two sets of strands 27 to create two curved joints 28, increasing the damping characteristic of the ring 25. In other variations the joint may have different shapes, such as straight, oval, round, triangular, jagged.

FIG. 45 describes a variation of the fourth embodiment, where one single ring 25 is configured with two sets of strands 27 to create two curved joints 28, increasing the dampening characteristic of the ring 25. In other variations the joint may have different shapes, such as straight, oval, round, triangular, jagged.

Figure 46:
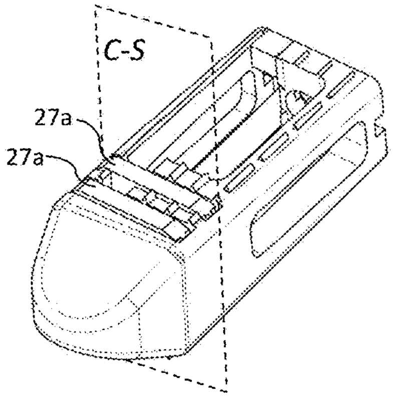
FIG. 46 represents a perspective front view of a classic PLIF or TLIF interbody cage with two split strands.
Figure 47:
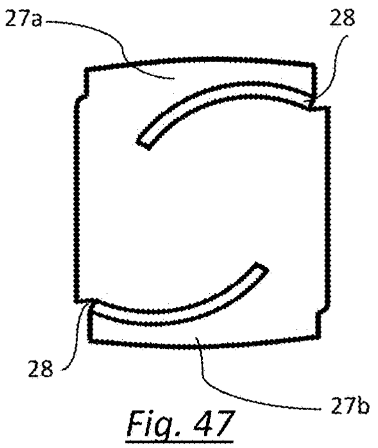
FIG. 47 represents a front view of a cross section "C-S" of the cage in FIG. 46 at the location of opposite split strands.

FIGS. 46 and 47 describe how the invention of the strands 27*a*, 27*b* and joints 28 may be applied to a standard interbody cage. FIG. 46 describes two strands 27*a* arranged on the upper surface of a standard interbody cage perpendicularly to the longitudinal axis, with two additional strands 27*b* arranged in the same axis on the lower surface of the cage (not shown on FIG. 46) and FIG. 47 represents a cross section of the cage at the location "C-S" of two opposite strands 27*a* and 27*b*, describing the two joints 28 of the invention. Several strands 27*a*, 27*b* may be arranged on the surfaces of the interbody cage with the curved joints 28, alternating with their opening towards one direction for one strand 27*a*, 27*b* and then with their opening towards the opposite direction for the next strand 27*a*, 27*b*; this offers a balanced surface of strands 27*a*, 27*b* against the compression force "F2" of the vertebrae V1, V2. In variations, the strands 27*a*, 27*b* may be positioned in different axes on the surfaces of the interbody cage, such as its longitudinal axis, or obliquely, or in a combination of a plurality of different axes.

Figure 40:
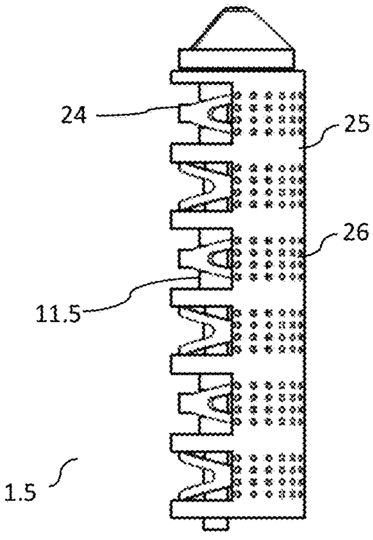
FIG. 40 represents a top view of the cage of the fourth embodiment in a stowed configuration.
Figure 41:
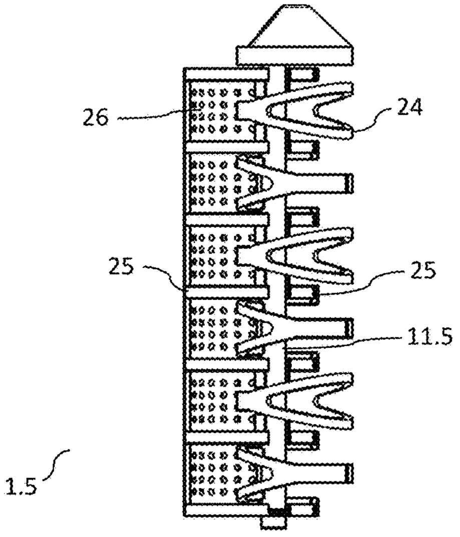
FIG. 41 represents a top view of the cage in FIG. 40 in a deployed configuration.
Figure 48:
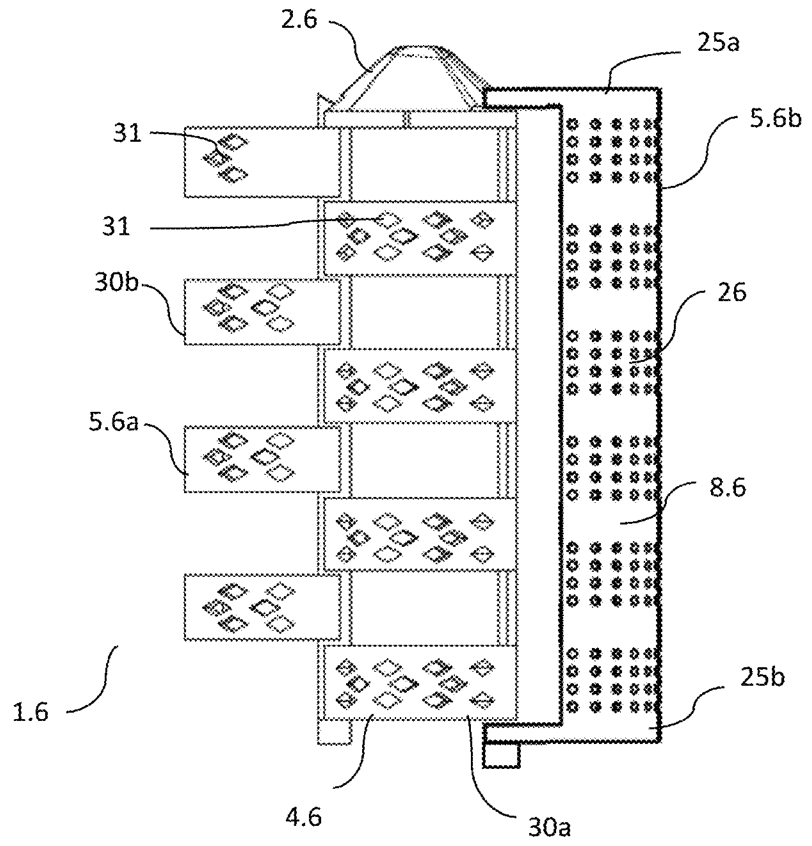
FIG. 48 represents a top view of a deployed cage comprising an open mesh structured extension member as variation of the fourth embodiment mounted on a mesh structured body and second extension member.
Figure 49:
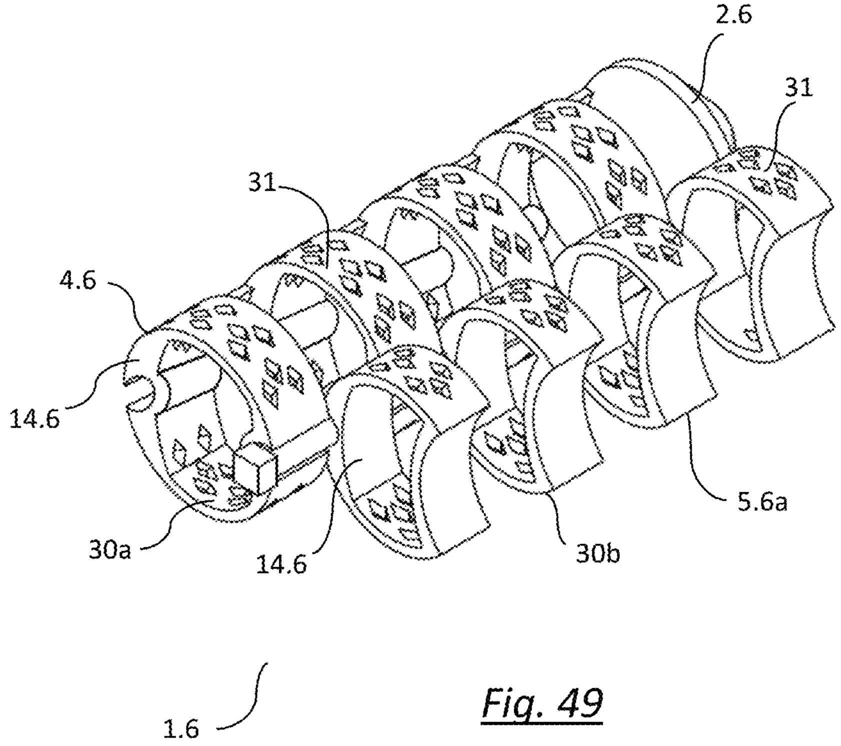
FIG. 49 represents the mesh-structured body and mesh-structured extension member of the cage in FIG. 48 in a deployed configuration.

FIGS. 48 and 49 describe a variation of the fourth embodiment, where the cage 1.6 comprises a body 4.6 and a first extension member 5.6*a*, both structured with aligned rings 30*a*. 30*b*, which are thin and wide like ribbons, and a second extension member 5.6*b*, which is configured with the same sheets of mesh 26 as in the variation represented in FIGS. 38, 40 and 42 and structured like the extension member 5.4 of the third embodiment shown in FIG. 30. As shown in FIG. 48, sheets of mesh 16 connect the two cambered structures 25*a*, 25*b* on the front and rear ends of the second extension member 5.6*b*, which are mounted on axes 11.4*b*. The surface of the second extension member 5.6*b*, between its front- and rear-ends may also be supported by cambered structures 8.6 connected one to another with sheets of mesh.

According to FIGS. 48 and 49, the ribbon-rings 30*a*, 30*b* mounted on the body 4.6 and on the first extension member 5.6*a* are punctured on their surfaces 31 which rest against the vertebrae after the deployment of the extension members: the number and size of punctures and the thickness, width and length of the ribbon-rings 30*a*, 30*b* on these punctured surfaces 31 define the degree of flexibility of these surfaces 31, between a very flexible structure like the mesh 26 structure of the second extension member 5.6*b*, ranging to a structure of an almost rigid cambered ribbon 8.6. The ribbon rings 30*a*, 30*b* have a strengthened structure 14.6 on their opposite sides which are perpendicular to the planes of the vertebrae V1, V2 when the cage 1.6 is deployed: these strengthened structures offer to the body 4.6 and to the first extension member 5.6*a* an increased resistance against the compression force "F2" of the vertebrae V1 and V2. The ribbon-rings 30*b* of the first extension member 5.6*b* have an inwardly cambered surface, which also enables to modulate the flexibility of the first extension member 5.6*a* and the damping characteristic of the whole cage 1.6. It addition, such inward curb reduces the lateral occupation space of such extension member 5.6*a*. In summary, the cage 1.6 of this variation of the fourth embodiment, while it is not configured with any split rings 24, 25 with strands 27 defining joints 28 as the cage 1.5 of the preceding variation, it may nevertheless oppose a flexible surface to comply with the irregular anatomy of the vertebral vertebral endplates V1, V2.

Figure 50:
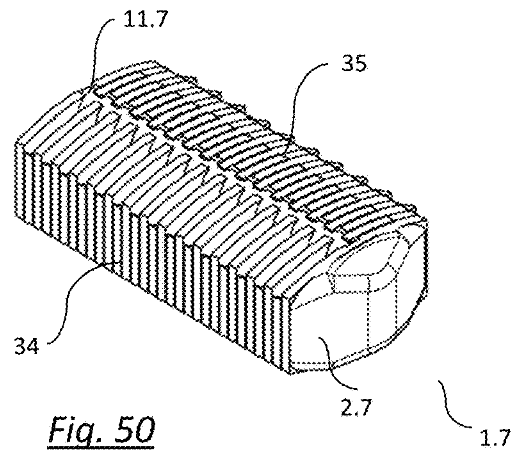
FIG. 50 represents a perspective front view of the cage of the fifth embodiment in a stowed configuration, with its large dimension surfaces facing upwards and downwards.
Figure 51:
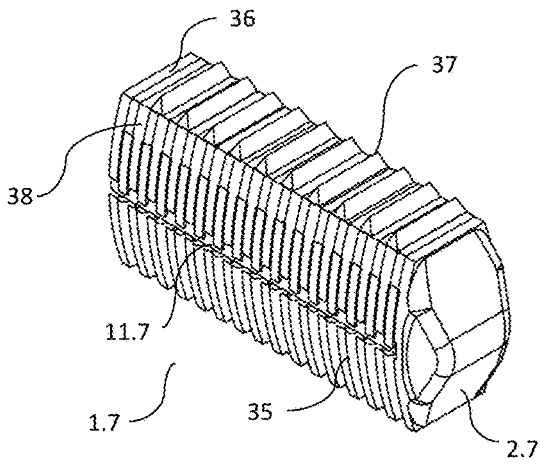
FIG. 51 represents a perspective front view of the same cage as in FIG. 50 after a 90° rotation, with its small dimension surfaces facing upwards and downwards.
Figure 52:
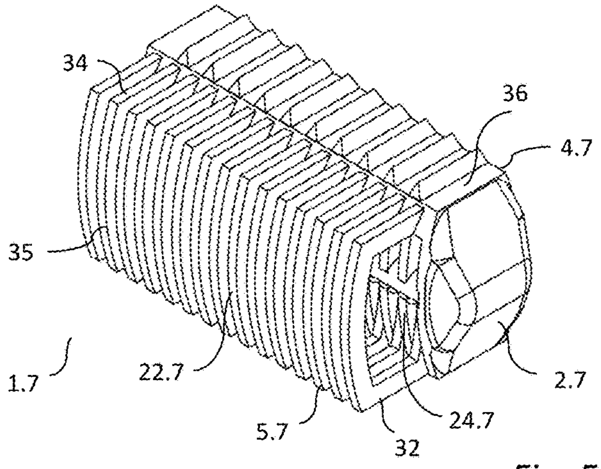
FIG. 52 represents a perspective front view of the cage of FIG. 51 in a deployed configuration.

FIGS. 50 to 52 represent the fifth embodiment of the invention of a cage 1.7 comprising a body 4.7 configured with parallel aligned rings 24.7 defining a parallelepiped shape. An extension member 5.7 with a front end 32 and a rear end 33 is configured with parallel aligned hooks 22.7 defining a second parallelepiped shape. Each of the parallelepiped body 4.7 and parallelepiped extension member 5.7 define two large-dimension surfaces 35 positioned in essentially parallel planes and two small-dimension surfaces 34 (which will also be named "Extremities") also positioned in essentially parallel planes. One of the small-dimension surfaces 34 of the rings 24.7 of the body 4.7 is coated with a layer 36 connecting the wedged front end 2.7 and flat rear end 3.7 of the body 4.7; anchoring means 37 are arranged on that layer 36. As shown in FIG. 51, a narrow portion of one large-dimension surface 35 of the body 4.7 is also coated with a narrow layer of material 38, towards the coated layer 36 on the small-dimension surface 34. The extension member 5.7 is mounted on a shaft 11.7 positioned ex-centrally from the median longitudinal axis of the extension member 5.7, near the periphery of one large-dimension surface 35 of the extension member 5.7. The shaft 11.7 is received in two channels **10.7*a*, 10.7*b* arranged on the body 4.7 ex-centrally from the medium longitudinal axis of said body 4.7**, near the periphery of one of its large-dimension surfaces.

As shown in FIGS. 50 and 51, in the stowed configuration of the cage 1.7, the parallel hooks 22.7 of the extension member 5.7 are partially wrapped in the coating layers 36, 38 arranged on the body 4.7 and are stowed between the parallel rings 24.7 of the body 4.7 into one single parallelepiped shaped cage 1.7. In FIG. 50, the cage is positioned with its large-dimension surfaces 35 facing upwards and downwards, which is the favored position for the insertion of the cage 1.7 between two adjoining vertebrae, while in FIG. 51, the cage is positioned after a 90° rotation, with its small-dimension surfaces 34, one of which is the coated surface 36, now facing upwards and downwards. FIG. 52 describes the cage 1.7 after the deployment of the extension member 5.7 outwards from the body 4.7.

Figure 55:
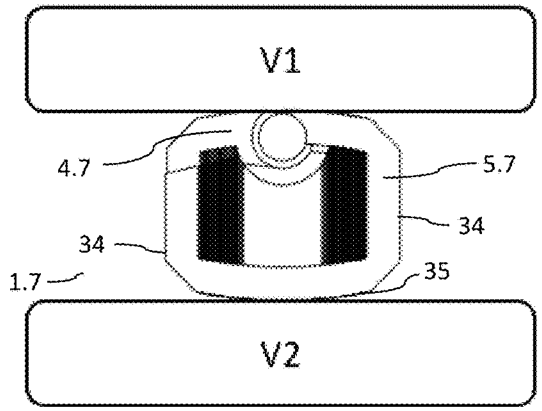
FIG. 55 represents a front view of a cross-section of the cage of the fifth embodiment in a stowed configuration between two schematic vertebrae
Figure 56:
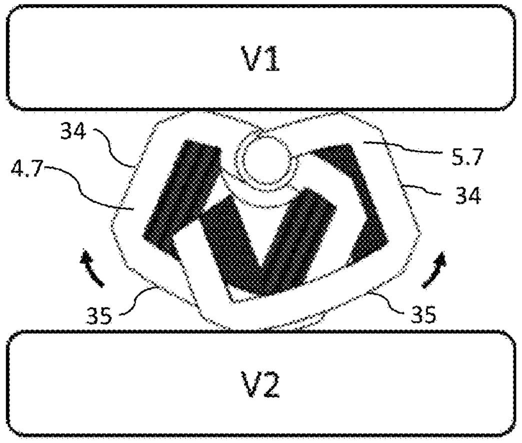
FIG. 56 represents the same front view of the cage as in FIG. 55 with a slightly pivoted body and slightly deployed extension member.
Figure 57:
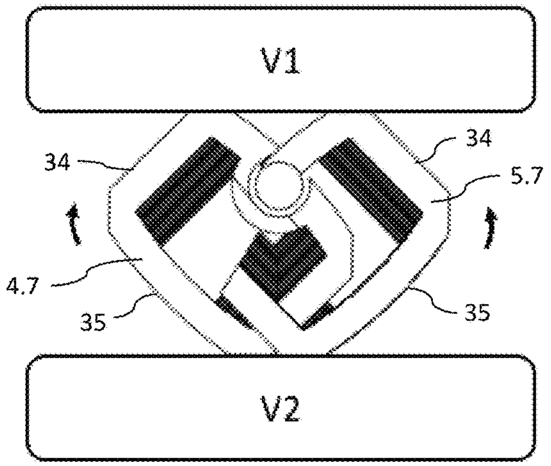
FIG. 57 represents the same front view of the cage as in FIG. 56 with a further pivoted body and further deployed extension member.
Figure 58:
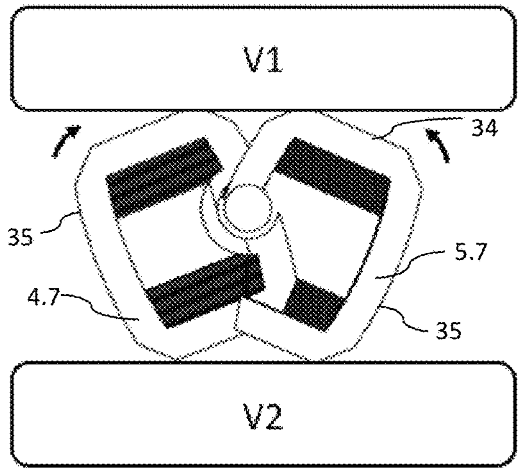
FIG. 58 represents the same front view of the cage as in FIG. 57 with a nearly fully pivoted body and deployed extension member.
Figure 59:
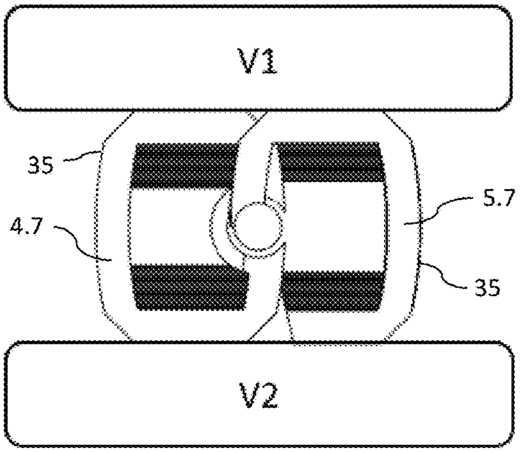
FIG. 59 represents the same front view of the cage as in FIGS. 55 to 57 with a fully pivoted body and deployed extension member.

The deployment of the cage 1.7 is described in FIGS. 55 to 59. As shown in FIG. 55, the cage 1.7 is first introduced between two vertebrae V1, V2 in a wrapped or stowed configuration, with the large dimension surfaces 35 of the body 4.7 and extension member 5.7 engaging said vertebrae and the separation space of the vertebrae V1, V2 substantially equal to the width of the small dimension surface 34. FIG. 56 describes the beginning of the pivoting of the extension member 5.7 relative to the reverse-pivoting of the body 4.7, with the respective Extremities 34 of the body 4.7 and of the extension member 5.7 disassembling. The motion of two respective Extremities 34 disassembling on one of the large dimension surfaces 35 entails, on the other side of the pivoting axis 11.7, the corresponding motion of the Extremities 34 disassembling on the other large dimension surfaces 35. The vertebrae V1, V2 are engaged by the four Extremities 34 and the pressure exerted by the four disassembling Extremities 34 against the Vertebrae V1, V2 spreads the space between the said two vertebrae. FIGS. 57 and 58 describe the progression of the disassembling of the two pairs of Extremities 34 of the body 4.7 and of the extension member 5.7 until the two small dimension surfaces or Extremities 34 of each of the body 4.7 and of the extension member 5.7 fully rest against the two opposite vertebrae V1, V2, as shown in FIG. 59, thus significantly increasing their separation space to the width of the large dimension surfaces 35. Each of the body 4.7 and the extension member 5.7 has pivoted approximately 90°. The deployed cage 1.7 has also laterally expanded in width by a factor of nearly two.

Figure 53:
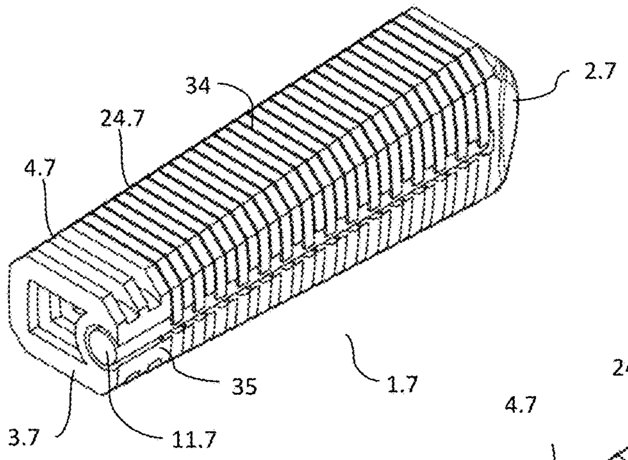
FIG. 53 represents a perspective rear view of a variation of the cage of the fifth embodiment with its small dimension surfaces defining angled planes.
Figure 54:
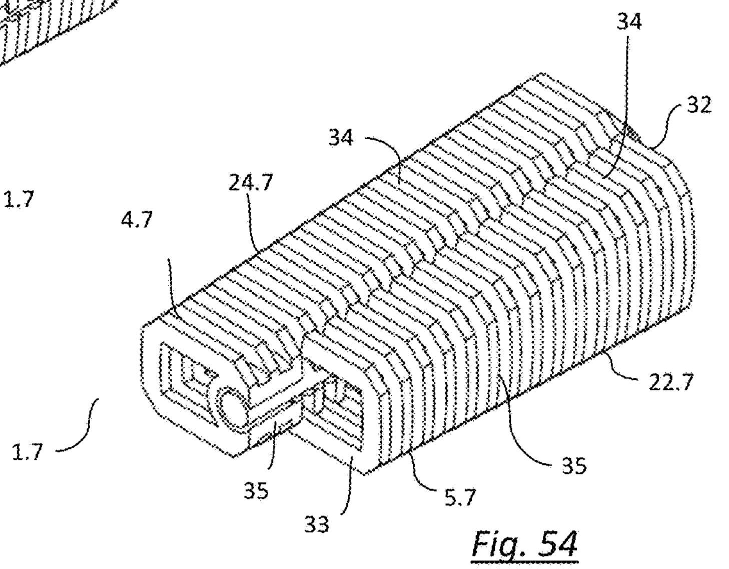
FIG. 54 represents a perspective rear view of the cage of FIG. 53 in a deployed configuration.

FIGS. 53 and 54 describe a variation of the fifth embodiment, with the body 4.7 of the cage 1.7 being configured with parallel rings 24.7 but without coated layers. Compared to the preferred fifth embodiment in FIGS. 50 to 52, the two pairs of small dimension surfaces 34 of the cage 1.7 of this variation are angled relative to each other, which is suitable for posterior, postero-lateral and transforaminal surgical approaches.

Figure 60:
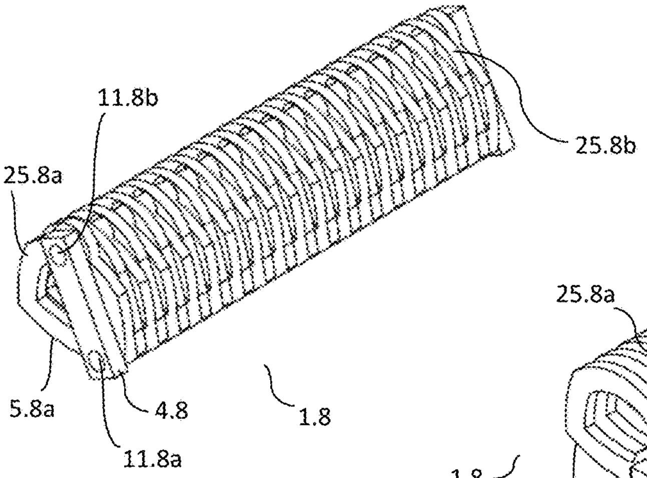
FIG. 60 represents a perspective front view of the cage of the sixth embodiment in a stowed configuration.
Figure 61:
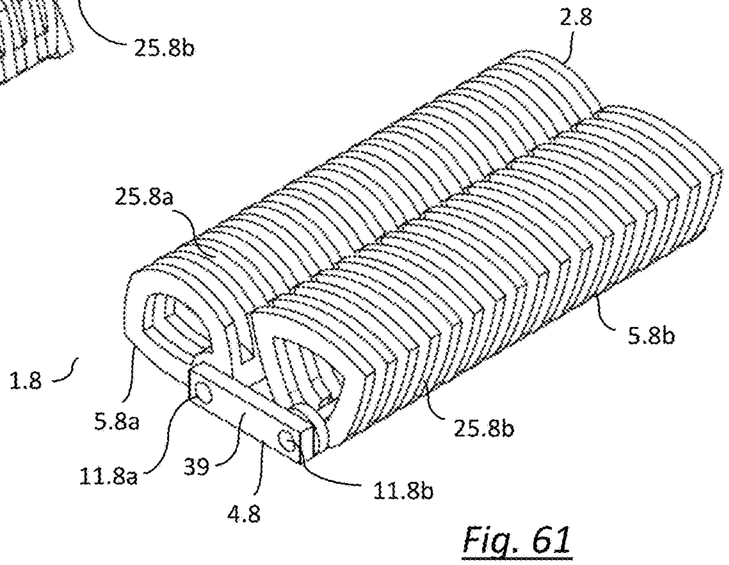
FIG. 61 represents a perspective front view of the same cage as in FIG. 60 in a deployed configuration.
Figure 62:
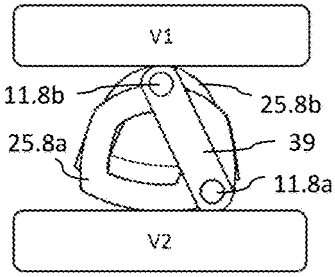
FIG. 62 represents a front view of the cage of the sixth embodiment in a stowed configuration between two schematic vertebrae.

FIGS. 60 and 61 represent the sixth embodiment of the invention, with a cage 1.8 having one body 4.8 consisting of two shafts **11.8*a*, 11.8*b* fixed to two plates 39 at the front and rear ends of the body 4.8. The shafts 11.8*a*, 11.8*b* of the body 4.8 are received within two respective channels 10.8*a*, 10.8*b* arranged asymmetrically on two extension members 5.8*a*, 5.8*b*. The extension members 5.8*a*, 5.9*b* are configured with parallel rings 25.8*a*, 25.8*b* with such parallel rings arranged to be stowed between each other in a stowed configuration of the cage 1.8 as shown in FIG. 60. FIG. 61 describes the cage 1.8 in a deployed configuration of the two extension members 5.8*a*, 5.8*b* and of the body 4.8, which has been pivoted approximately 110°-120° around the axis of its shaft 11.8*a***.

Figure 63:
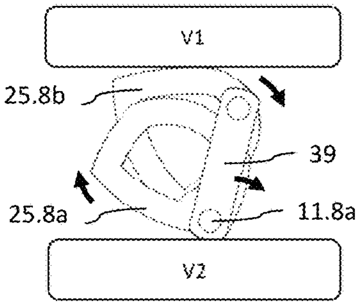
FIG. 63 represents the same front view of the cage as in FIG. 62 with deploying extension members and pivoting body.
Figure 64:
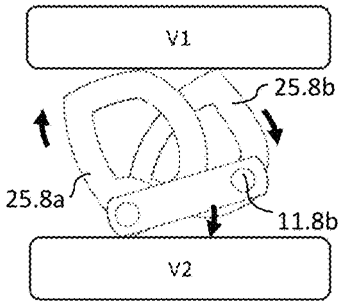
FIG. 64 represents the same front view of the cage as in FIGS. 62 and 63 with further deploying extension members in the same direction and a further pivoting body.
Figure 65:
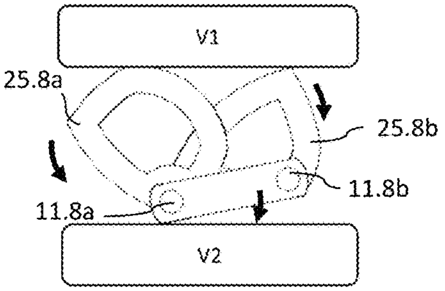
FIG. 65 represents the same front view of the cage as in FIGS. 62 to 64 with the further deployment of one extension member in one direction, the further deployment of the other extension member in the reverse direction and the further pivoting of the body.
Figure 66:
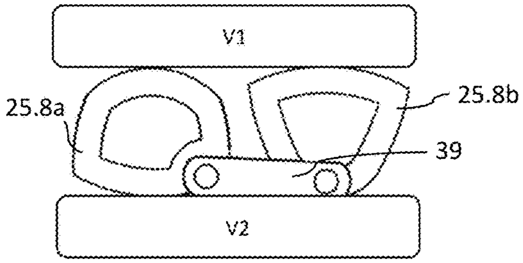
FIG. 66 represents the same front view of the cage as in FIGS. 62 to 65 with two fully deployed extension members.

The method of deployment of the cage 1.8 of the sixth embodiment is described in FIGS. 62 to 66. According to FIG. 62, the cage 1.8 is introduced between two vertebrae V1, V2 in its stowed configuration. In variations of the method, the cage 1.8 may be introduced in any different positions of the stowed configuration. FIGS. 63 to 65 describe the deployment of the extension members **5.8*a*, 5.8*b*: they are rotated around the axes of the shafts 11.8*a*, 11.8*b* while the plates 39 of the body 4.8 connecting such shafts are also pivoted, and these motions distract the upper and lower vertebrae V1, V2 during the deployment. This multiple articulation with several joints enables the deployment asymmetrically of the three components of the cage 1.8. FIGS. 63 and 64 describe the pivoting of the rings 25.8*a* of the extension member 5.8*a* to support the spreading of the vertebrae V1, V2, but in different variations of the method, that extension member 5.8*a* could have stayed static while only the second extension member 5.8*b* and the body 4.8 are deploying. The deployment sequence described in FIGS. 63 to 65 is only an example to enable the invention, and there is a variety of sequences of deployment of the three components 4.8, 5.8*a*, 5.8*b* of the cage 1.8 of the sixth embodiment. FIG. 66 shows the cage 1.8** in its deployed configuration, with a lateral expansion factor in excess of two.

All embodiments of the invention are configured to self-lock in the deployed configuration of the extension member 5 by the compression force "F2" of the vertebrae V1, V2. Any additional suitable technical means of locking the extension member 5 into a deployed position may be applied to the invention. The Figures describe extension members 5 whose shafts 11 or channels 10 are arranged within the perimeter of the surfaces of the bodies 4 or extension member 5. In different variations of the invention, the channels 10 or shafts 11 may be configured on the body 4 or the extension member 5 beyond the perimeter of their surfaces.

It goes without saying that each of the characteristics of each embodiment and any of its variations may be applied to any other embodiment or any of their variations. In variations of any embodiment, the shafts 11 and channels 10 may be angled obliquely compared to the longitudinal axes of the cage 1, so as to introduce differential deployment dimensions for the cambered ribbons 8, 12, discs **15*a*, 15*b***, 15c, blocks 5.2, hooks 22 and rings 24, 25 which are mounted on an obliquely positioned shaft 11 of an extension member 5 or a body 4. The bodies 4 of the cages 1 of the first to sixth embodiments and the extension members 5 may be made in different materials.

The embodiments of the invention may apply to any implants separating and/or fusing vertebrae, whether interbody implants, vertebral body replacement implants, interspinous implants and artificial discs. The invention may also apply to the reduction and/or fusion of other bones, such as the hips, the pelvis, and any long bones and joints.

The embodiments of the invention may apply to human spinal columns and to animal spinal columns.

What is claimed is:

1. A dynamically deployable intervertebral implantable device with a configurable structure having at least one pivotable and stowable component, the device comprising:

a plurality of first projection elements formed on a common base on at least one surface of a geometric body defined by contiguous surfaces;

a plurality of second projection elements arranged on the at least one pivotable and stowable component being pivotably and modularly coupled to the at least one surface of the geometric body, forming one of a plurality of cantilevered or fixed structures having one of enclosed, open and or multi columnar structures, and each of the plurality of second projection elements being configured to pivotably stow within the geometric body by engaging with and forming a structured and scalable structure intersecting with the corresponding first projection elements of the geometric body forming a compact first form factor for implant between an upper and lower vertebrae, and forming a second form factor when the second projection elements are unstowed extending outward, increasing the perimeter of the contact surface between the device and vertebral endplates of an upper and lower vertebrae.

2. The device of claim 1, wherein the at least one pivotable and stowable component includes at least one extension member pivotably coupled to the geometric body about a pivot axis such that the at least one extension member and the plurality of second projection elements formed thereon, pivots about the pivot axis extending along at least a portion of the longitudinal length of the geometric body, and wherein the plurality of first and second projection elements form one of a plurality of cantilevered or fixed structures having one of enclosed, open and or multi columnar structures providing adjustable load bearing areas to enable segment stabilization between the upper and lower vertebrae within an intervertebral space therebetween.

3. The device of claim 2, wherein the geometric body comprises a front end and a rear end, wherein a first channel section and a second channel section are arranged between the front end and the rear end of the geometric body, the first channel section and the second channel section being coaxial and respectively receiving pivoting shaft sections of the at least one extension member such that the at least one extension member pivots about the pivot axis extending along at least a portion of the longitudinal length of the geometric body; and wherein the geometric body and the at least one extension member form a modularly connected and buildable device offering structural flexibility to add, remove or rearrange modules to adapt to various vertebral bone anomalies such as one of structural deterioration of spinal disc desiccation and other various metabolic bone disease, presenting varying mechanical stresses.

4. The device of claim 1, wherein the plurality of first and second projection elements form a plurality of structures having variable flexing strengths, to enable segment stabilization between the upper and lower vertebrae, and being modularly custom designed to accommodate patient specific requirements.

5. An implantable device for insertion between vertebral bodies, the device comprising:

a) a geometric body, wherein the geometric body is dynamically scalable in structure and being modularly configurable to transform from a first form factor to a second form factor;

b) a plurality of first projection elements formed on a common base on at least one surface of the geometric body, wherein the plurality of first projection elements being an integral part of the geometric body;

c) at least one extendable and stowable component coupled pivotably with the at least one surface of the geometric body, the at least one extendable and stowable component having a plurality of second projection elements forming one of a plurality of cantilevered or fixed structures having one of enclosed, open and or multi columnar structures, d) wherein, in a stowed configuration, each of the plurality of second projection elements is configured for stowage within the geometric body by intersecting with the plurality of first projection elements and compose the first form factor for implantation;

e) whereupon in an unstowed configuration, the plurality of second projection elements extend outwardly, increasing the perimeter of the contact surface between the device and vertebral endplates of an upper and lower vertebrae, dovetailing with corresponding first projection elements of the geometric body, thereby transitioning the device to the second form factor, engineered to accommodate a larger coverage area and volume in the second form factor that is larger than a coverage area and volume in the first form factor within an intervertebral space; and f) wherein in both the stowed configuration and the unstowed configurations, the device maintains its structural integrity and ductility while maintaining effective support between the vertebral bodies.

6. The implantable device of claim 5, wherein the geometric body and the plurality of first projection elements include flexible and ductile structures for damping, load sharing, resilient deformation and flexible vertebral interface to absorb and distribute applied loads due to compressive loads between the intervertebral space at an implant site.

7. The implantable device of claim 5, wherein the plurality of second projection elements interact with the plurality of first projection elements in a manner forming a secure and stable enlarged surface area, when in the second form factor, thereby preventing inadvertent detachment or displacement post-implantation.

8. The implantable device of claim 5, wherein the at least one extendable and stowable component, and the plurality of second projection elements formed thereon, pivots about an axis extending along a longitudinal length of the geometric body between a stowed configuration and an unstowed configuration, and wherein the geometric body is wrapped around the extendable and stowable component in a first configuration and unwrapped from the geometric body in a second configuration; and wherein the geometric body and the at least one extendable and stowable component are manufactured in a variety of sizes and dimensions to accommodate a range of intervertebral spaces, ensuring a dimensioned fit for individual patient anatomies.

9. The implantable device of claim 5, wherein the device is configured to facilitates minimally invasive insertion to transition from the first form factor to the second form factor dynamically, promoting quicker recovery times and reduced surgical risk.

10. A dynamically deployable intervertebral implantable device comprising:

a geometric body having defined surfaces;

a plurality of cantilevered projection elements having a fixed end attached to the defined surfaces of the geometric body and distributed along a longitudinal length of the geometric body, wherein the plurality of cantilevered projection elements are formed on at least one surface of the defined surfaces of the geometric body; and wherein the plurality of cantilevered projection elements, initially exhibiting a first form factor, are resiliently adjustable to assume a second form factor when subjected to a vertebral compressive load generated between an upper and lower vertebrae, such that a free end of the projection elements forms resiliently deformable load bearing regions; and wherein in the second form factor the plurality of cantilevered projection elements extend outward to increase the perimeter of the contact surface between the device and vertebral endplates of the upper and lower vertebrae.

11. The dynamically deployable intervertebral implantable device of claim 10, wherein the plurality of cantilevered projection elements transition from the first form factor to the second form factor by movement about an axis extending along the longitudinal length of the geometric body; and wherein the second form factor is larger in volume than the first form factor.

12. The dynamically deployable intervertebral implantable device of claim 10, wherein the transition from the first form factor to the second form factor is one of linearly and non-linearly responsive to the magnitude of the vertebral compressive load that maintains the plurality of cantilevered projection elements in the second form factor.

13. The dynamically deployable intervertebral implantable device of claim 10, wherein the variable load bearing regions the resiliently deformable load bearing regions are configured to distribute loads across a vertebral interface to mimic physiological and anatomical load distribution.

14. The dynamically deployable intervertebral implantable device of claim 10, further comprising a bone fusion material within or around the plurality of cantilevered projection elements.

15. The dynamically deployable intervertebral implantable device of claim 10, wherein the geometric body includes a unique configuration of the plurality of cantilevered projection elements on both an upper and corresponding lower surface of the defined surfaces of the geometric body.

16. The dynamically deployable intervertebral implantable device of claim 10, wherein the second form factor is pre-configured based on desired biomechanical properties of the intervertebral implantable device implant in an implanted state.

17. The dynamically deployable intervertebral implantable device of claim 10, wherein a plurality of structurally tailored first projection elements are formed on at least one surface of the defined surfaces of the geometric body, wherein the plurality of first projections elements adaptively support different load conditions dictated by patient-specific needs.

18. The dynamically deployable intervertebral implantable device of claim 10, wherein the plurality of structurally tailored first projections elements are designed based on biomechanical studies and simulations to support a range of vertebral load conditions.

19. The dynamically deployable intervertebral implantable device of claim 10, wherein the plurality of structurally tailored first projection elements are customizable based on a patient's weight, physical activity level, location of implantation and to adapt to various vertebral bone anomalies such as one of structural deterioration of spinal disc desiccation or other various metabolic bone disease, presenting varying mechanical stresses.

20. The dynamically deployable intervertebral implantable device of claim 10, wherein the geometric body includes one of a prismatic body, conical body, cylindrical body, and a combination thereof.

* * * * *